(12) United States Patent
Gerner et al.

(10) Patent No.: US 8,329,636 B2
(45) Date of Patent: Dec. 11, 2012

(54) CARCINOMA DIAGNOSIS AND TREATMENT, BASED ON ODC1 GENOTYPE

(75) Inventors: Eugene Gerner, Tucson, AZ (US); Jason A. Zell, Dana Point, CA (US); Christine McLaren, Irvine, CA (US); Frank Meyskens, Irvine, CA (US); Hoda Anton-Culver, Irvine, CA (US); Patricia A. Thompson, Tucson, AZ (US)

(73) Assignees: Arizona Board of Regents on Behalf of University of Arizona, Tucson, AZ (US); The Regents of the University of California, a California Corporation, Oakland, CA (US)

( * ) Notice: Subject to any disclaimer, the term of this patent is extended or adjusted under 35 U.S.C. 154(b) by 246 days.

(21) Appl. No.: 12/780,592

(22) Filed: May 14, 2010

(65) Prior Publication Data

US 2010/0317708 A1    Dec. 16, 2010

Related U.S. Application Data

(60) Provisional application No. 61/217,682, filed on Jun. 3, 2009, provisional application No. 61/217,679, filed on Jun. 3, 2009, provisional application No. 61/216,216, filed on May 14, 2009.

(51) Int. Cl.
*A01N 61/00* (2006.01)
(52) U.S. Cl. .......................................................... 514/1
(58) Field of Classification Search ........................ None
See application file for complete search history.

(56) References Cited

U.S. PATENT DOCUMENTS

| | | | | |
|---|---|---|---|---|
| 4,330,559 | A | 5/1982 | Bey et al. | 514/564 |
| 4,413,141 | A | 11/1983 | Bey et al. | 562/561 |
| 5,814,625 | A | 9/1998 | Larson et al. | 514/171 |
| 5,843,929 | A | 12/1998 | Larson et al. | 514/182 |
| 6,258,845 | B1 | 7/2001 | Gerner et al. | 514/544 |
| 7,592,319 | B2 | 9/2009 | Li et al. | 514/44 |
| 2005/0032726 | A1* | 2/2005 | Li et al. | 514/44 |

OTHER PUBLICATIONS

Basuroy et al (J Biochem, 2006, 139: 27-33).*
Alberts et al., "Do NSAIDs exert their colon cancer chemoprevention activities through the inhibition of mucosal prostaglandin synthetase?," *J. Cell. Biochem. Supp.*, (22):18-23, 1995.
Babbar et al., "Induction of spermidine/spermine N1-acetyltransferase (SSAT) by aspirin in Caco-2 colon cancer cells," *Biochem. J.*, 394:317-24, 2006.
Barry et al., "Ornithine decarboxylase polymorphism modification of response to aspirin treatment for colorectal adenoma prevention," *J. Natl. Cancer Inst.*, 98(20):1494-500, 2006.
Basuroy and Gerner, "Emerging concepts in targeting the polyamine metabolic pathway in epithelial cancer chemoprevention and chemotherapy," *J. Biochem.*, 139:27-33, 2006.
Bedi et al., "Inhibition of apoptosis during development of colorectal cancer," *Cancer Res.*, 55(9):1811-1816, 1995.
Bello-Fernandez et al., "The ornithine decarboxylase gene is a transcriptional target of c-Myc," *Proc. Natl. Acad.. Sci. USA*, 90:7804-8, 1993.
Childs et al., "Polyamine-dependent gene expression," *Cell. Molec. Life Sci.*, 60:1394-1406, 2003.
Derynck et al., "TGF-beta signaling in tumor suppression and cancer progression," *Nature Genetics*, 29:117-29, 2001.
DuBois et al., "G1 delay in cells overexpressing prostaglandin endoperoxide synthase-2," *Cancer Res.*, 56:733-737, 1996.
Erdman et al., "APC-dependent changes in expression of genes influencing polyamine metabolism, and consequences for gastrointestinal carcinogenesis, in the *Min* mouse ," *Carcinogenesis*, 20(9):1709-13, 1999.
Fultz and Gerner, "APC-dependent regulation of ornithine decarboxylase in human colon tumor cells," *Mol. Carcinog.*, 34:10-8, 2002.
Gerner and Meyskens, "Polyamines and cancer: old molecules, new understanding," *Nature Rev. Cancer*, 4:781-92, 2004.
Giardiello et al., "Ornithine decarboxylase and polyamines in familial adenomatous polyposis," *Cancer Res.*, (57):199-201, 1997.
Guo et al., "Functional analysis of human ornithine decarboxylase alleles," *Cancer Res.*, 60(22):6314-6317, 2000.
Hanif et al., "Effects of nonsteroidal anti-inflammatory drugs on proliferation and on induction of apoptosis in colon cancer cells by a prostaglandin-independent pathway," *Biochemical Pharmacology*, (52):237-245, 1996.
Hubner et al., "Ornithine decarboxylase G316A genotype is prognostic for colorectal adenoma recurrence and predicts efficacy of aspirin chemoprevention," *Clin. Cancer Res.*, 14(8):2303-9, 2008.
Ignatenko et al., "Role of c-Myc in intestinal tumorigenesis of the ApcMin/+ mouse," *Cancer Biol. Ther.*, 5(12):1658-64, 2006.
International Search Report and Written Opinion, issued in International application No. PCT/US10/34974, dated Jul. 2, 2010.
Iwamoto et al., "Expression of beta-catenin and full-length APC protein in normal and neoplastic colonic tissues," *Carcinogenesis*, 21:1935-40, 2000.
Kingsnorth et al., "Effects of alpha-difluoromethylornithine and 5-fluorouracil on the proliferation of a human colon adenocarcinoma cell line," *Cancer Res.*, 43(9):4035-8, 1983.
Kruh et al., "Expression Pattern of MRP in Human Tissues and Adult Solid Tumor Cell Lines," *J. Natl. Cancer Inst.*, 87(16):1256-1258, 1995.
Ladenheim et al., "Effect of sulindac on sporadic colonic polyps," *Gastroenterology*, 108:1083-1087, 1995.

(Continued)

*Primary Examiner* — Sean Aeder
(74) *Attorney, Agent, or Firm* — Parker Highlander PLLC

(57) ABSTRACT

The present invention provides methods and kits a) for predicting colorectal cancer patient survival, as well as the survival of patients harboring other invasive cancers where cellular proliferation and carcinogenesis is linked, in part, to high levels of ODC activity and increased cellular polyamine contents, and b) for selecting the corresponding treatment options for such patients based on the allelic nucleotide sequence or SNP at position +316 of the ODC1 promoter gene as well as cancer treatment methods, in each case, which include the determination of the ODC1 promoter +316 position genotype, as a means to guide treatment selection.

33 Claims, 11 Drawing Sheets

OTHER PUBLICATIONS

Lanza et al., "Peptic ulcer and gastrointestinal hemorrhage associated with nonsteroidal anti-inflammatory drug use in patients younger than 65 years. A large health maintenance organization cohort study," *Arch. Intern. Med.*, 155:1371-1377, 1995.

Le et al., "Effects of socioeconomic status and treatment disparities in colorectal cancer survival," *Cancer Epidemiol. Biomarkers Prev.*, 17:1950-62, 2008.

Lipkin, "New rodent models for studies of chemopreventive agents," *J. Cell Biochem. Suppl.*, 28-29:144-7, 1997.

Love et al., "Randomized phase I chemoprevention dose-seeking study of alpha-difluoromethylornithine," *J. Natl. Cancer Inst.*, 85:732-7, 1993.

Luk and Baylin, "Ornithine decarboxylase as a biologic marker in familial colonic polyposis," *N. Engl. J. Med.*, 311(2):80-83, 1984.

Lupulescu, "Control of precancer cell transformation into cancer cells: its relevance to cancer prevention," *Cancer Detect. Prev.*, 20(6):634-637, 1996.

Martinez et al., "Pronounced reduction in adenoma recurrence associated with aspirin use and a polymorphism in the ornithine decarboxylase gene," *Proc. Natl. Acad. Sci. USA*, 100:7859-64, 2003.

Matsubara et al., "Association between high levels of ornithine decarboxylase activity and favorable prognosis in human colorectal carcinoma," *Clinical Cancer Res.*, 1:665-71, 1995.

McLaren et al., "Longitudinal assessment of air conduction audiograms in a phase III clinical trial of difluoromethylornithine and sulindac for prevention of sporadic colorectal adenomas," *Cancer Prev. Res.*, 1(7):514-21, 2008.

Meyskens et al., "Difluoromethylornithine plus sulindac for the prevention of sporadic colorectal adenomas: a randomized placebo-controlled, double-blind trial," *Cancer Prev. Res.*, 1(1):32-8, 2008.

Meyskens et al., "Dose de-escalation chemoprevention trial of alpha-difluoromethylornithine in patients with colon polyps," *J. Natl. Cancer Inst.*, 86(15):1122-1130, 1994.

Meyskens et al., "Effect of alpha-difluoromethylornithine on rectal mucosal levels of polyamines in a randomized, double-blinded trial for colon cancer prevention," *J. Natl. Cancer Inst.*, 90(16):1212-8, 1998.

Muscat et al., "Nonsteroidal antiinflammatory drugs and colorectal cancer," *Cancer*, 74:1847-1854, 1994.

O'Brien et al., "Differences in ornithine decarboxylase and androgen receptor allele frequencies among ethnic groups," *Molec. Carcinog.*, 41(2):120-3, 2004.

Pardali and Moustakas, "Actions of TGF-beta as tumor suppressor and pro-metastatic factor in human cancer," *Biochimica et Biophysica Acta*, 1775:21-62, 2007.

Peel et al., "Characterization of hereditary nonpolyposis colorectal cancer families from a population-based series of cases," *J. Natl. Cancer Inst.*, 92:1517-22, 2000.

Pegg, "Recent advances in the biochemistry of polyamines in eukaryotes," *Biochem.*, 234(2):249-262, 1986.

Piazza et al., "Antineoplastic drugs sulindac sulfide and sulfone inhibit cell growth by inducing apoptosis," *Cancer Res.*, (55):3110-3116, 1995.

Piazza et al., "Apoptosis primarily accounts for the growth-inhibitory properties of sulindac metabolites and involves a mechanism that is independent of cyclooxygenase inhibition, cell cycle arrest, and p53 induction," *Cancer Res.*, (57):2452-2459, 1997a.

Piazza et al., "Sulindac sulfone inhibits azoxymethane-induced colon carcinogenesis in rats without reducing prostaglandin levels," *Cancer Res.*, (57):2909-2915, 1997b.

Pollard and Luckert, "Prevention and treatment of primary intestinal tumors in rats by piroxicam," *Cancer Res.*, 49:6471-6473, 1989.

Rao et al., "Chemoprevention of colon carcinogenesis by sulindac, a nonsteroidal anti-inflammatory agent," *Cancer Res.*, (55):1464-1472, 1995.

Reddy et al., "Dose-related inhibition of colon carcinogenesis by dietary piroxicam, a nonsteroidal antiinflammatory drug, during different stages of rat colon tumor development," *Cancer Res.*, 47:5340-5346, 1987.

Roberts and Wakefield, "The two faces of transforming growth factor beta in carcinogenesis," *Proc. Natl. Acad. Sci. USA*, 100:8621-3, 2003.

Seiler and Knodgen, "High-performance liquid chromatographic procedure for the simultaneous determination of the natural polyamines and their monoacetyl derivatives," *J.Chromatogr.*, 221(2):227-235, 1980.

Simoneau et al., "Alpha-difluoromethylornithine and polyamine levels in the human prostate: results of a phase IIa trial," *J. Natl. Cancer Inst.*, 93:57-9, 2001.

Simoneau et al., "The effect of difluoromethylornithine on decreasing prostate size and polyamines in men: results of a year-long phase IIb randomized placebo-controlled chemoprevention trial," *Cancer Epidemiol. Biomarkers Prev.*, 17:292-9, 2008.

Singh and Reddy, "Molecular markers in chemoprevention of colon cancer. Inhibition of expression of ras-p21 and p53 by sulindac during azoxymethane-induced colon carcinogenesis," *Annals. NY Acad. Sci.*, (768):205-209, 1995.

Singh et al., "Modulation of azoxymethane-induced mutational activation of ras protooncogenes by chemopreventive agents in colon carcinogenesis," *Carcinogenesis*, (15):1317-1323, 1994.

Tempero et al., "Chemoprevention of mouse colon tumors with difluoromethylornithine during and after carcinogen treatment," *Cancer Res.*, 49(21):5793-7, 1989.

Thomas and Thomas, "Polyamine metabolism and cancer," *J. Cell Mol. Med.*, 7:113-26, 2003.

U.S. Appl. No. 61/345,048 entitled "Cancer Prevention and Treatment Methods Based on Dietary Polyamine Content," submitted May 14, 2010.

Vane and Botting, "Mechanism of action of anti-inflammatory drugs," *Scand. J. Rheumatol.*, 25(Suppl. 102):9-21, 1996.

Visvanathan et al., "Association among an ornithine decarboxylase polymorphism, androgen receptor gene (CAG) repeat length and prostate cancer risk," *J. Urol.*, 171(2 Pt 1):652-5, 2004.

Wallace, "The physiological role of the polyamines," *Eur. J. Clin. Invest.*, 30:1-3, 2000.

Zell et al., "Associations of a polymorphism in the ornithine decarboxylase gene with colorectal cancer survival," *Clin. Cancer Res.*, 15(19):6208-16, 2009.

Zell et al., "Risk and risk reduction involving arginine intake and meat consumption in colorectal tumorigenesis and survival," *Intl. J. Cancer*, 120:459-68, 2007.

Zell et al., "Risk of cardiovascular events in a randomized placebo-controlled, double-blind trial of difluoromethylornithine plus sulindac for the prevention of sporadic colorectal adenomas," *Cancer Prev. Res.*, 2(3):209-12, 2009.

Zell et al., "Survival after colorectal cancer diagnosis is associated with colorectal cancer family history," *Cancer Epidemiol. Biomarkers Prev.*, 17:3134-40, 2008.

Ziogas and Anton-Culver, "Validation of family history data in cancer family registries," *Am. J. Prev. Med.*, 24:190-8, 2003.

Zell et al., "Ornithine decarboxylase-1 polymorphism, chemoprevention with eflornithine and sulindac, and outcomes among colorectal adenoma patients," *J. Natl. Cancer Inst.*, 102:1513-1516, 2010.

* cited by examiner

SEQUENCE LISTING

<160> NUMBER OF SEQ ID NOS: 5

<210> SEQ ID NO 1
<211> LENGTH: 21
<212> TYPE: DNA
<213> ORGANISM: Artificial Sequence
<220> FEATURE:
<223> OTHER INFORMATION: Synthetic Primer

<400> SEQUENCE: 1

```
tctgcgcttc cccatggggc t                                              21

<210> SEQ ID NO 2
<211> LENGTH: 15
<212> TYPE: DNA
<213> ORGANISM: Artificial Sequence
<220> FEATURE:
<223> OTHER INFORMATION: Synthetic Primer

<400> SEQUENCE: 2
tttcccaacc cttcg                                                     15

<210> SEQ ID NO 3
<211> LENGTH: 17
<212> TYPE: DNA
<213> ORGANISM: Artificial Sequence
<220> FEATURE:
<223> OTHER INFORMATION: Synthetic Primer

<400> SEQUENCE: 3
cctgggcgct ctgaggt                                                   17

<210> SEQ ID NO 4
<211> LENGTH: 17
<212> TYPE: DNA
<213> ORGANISM: Artificial Sequence
<220> FEATURE:
<223> OTHER INFORMATION: Synthetic Primer

<400> SEQUENCE: 4
aggaagcggc gcctcaa                                                   17

<210> SEQ ID NO 5
<211> LENGTH: 42
<212> TYPE: DNA
<213> ORGANISM: Artificial Sequence
<220> FEATURE:
<223> OTHER INFORMATION: Synthetic Primer

<400> SEQUENCE: 5
gcacgtgtgc ggcgcgcctc gccggcctgc ggagacacgt gg                       42
```

CARCINOMA DIAGNOSIS AND TREATMENT, BASED ON ODC1 GENOTYPE

The present application claims the benefit of priority to U.S. Provisional Application Nos. 61/217,682, filed Jun. 3, 2009, 61/217,679, filed Jun. 3, 2009, and 61/216,216, filed May 14, 2009, the entire contents of each of which are incorporated by reference herein.

This invention was made with government support under grants CA72008 (EWG), CA78134 (HAC), CA78285 (HAC), and CA95060 (EWG) from the National Institute of Health, contracts N01-PC-35136, N01-PC-35139 and N01-PC-54404 from the National Cancer Institute and agreement 1U58DP00807-01 from the Centers for Disease Control and Prevention. The government has certain rights in the invention.

BACKGROUND OF THE INVENTION

I. Field of the Invention

The present invention relates generally to the fields of cancer biology and medicine. More particularly, it concerns methods for the diagnosis, prevention and treatment of carcinomas and risk factors thereof.

II. Description of Related Art

A major impediment to the translation of cancer chemoprevention research into clinical practice has been marginal agent efficacy and toxicities that exceed benefit (Psaty and Potter, 2006; Lippman, 2006). For example, the demonstrated marked efficacy of polyamine-inhibitory combination of long-term daily oral D,L-α-difluoromethylornithine (DFMO, eflornithine) and sulindac among colorectal adenoma (CRA) patients was recently demonstrated (Meyskens et al., 2008), however, treatment was associated with modest, subclinical ototoxicity (McLaren et al., 2008), and a greater number of cardiovascular events among patients with high baseline cardiovascular risk (Zell et al., 2009). Identifying genetic features that identify the suitability of a patient for a given preventative or curative treatment regime would be a major benefit.

For example, there remains a need for effective and less toxic methods for treating and preventing colorectal cancers and other carcinomas. According to the National Cancer Institute, there were approximately 147,000 new cases and 50,000 deaths from colorectal cancer in the United States in 2009. Current treatment protocols, especially those for colon cancers and polyps, include tumor resection, chemotherapy and radiation therapy. A single nucleotide polymorphism (SNP) in intron-1 of the human ODC1 gene affects ODC1 transcription (Guo et al., 2000), and has been investigated as a genetic marker for colorectal adenoma (CRA) risk (Martinez et al., 2003; Barry et al., 2006; Hubner et al., 2008). The reported minor A-allele frequency is approximately 25% and despite differences across race/ethnicity, ODC1 genotype distribution is in Hardy-Weinberg equilibrium within each race (O'Brien et al., 2004; Zell et al., 2009). Individuals homozygous for the ODC1 minor A-allele have reduced risk of adenoma recurrence compared to those with the major G-allele (Martinez et al., 2003; Hubner et al., 2008). Furthermore, the ODC1 A-allele (AA or GA genotype, but not GG genotype) and reported aspirin usage have been associated with reduced colon polyp recurrence (Martinez et al., 2003; Barry et al., 2006; Hubner et al., 2008), and a statistically significant 50% reduced risk of advanced adenomas (Barry et al., 2006). Whether the ODC1 genotype differentially affects adenoma recurrence, tissue polyamine responses, toxicity profiles and how it may be used to determine the suitability of preventative and curative treatments would be a major advantage.

SUMMARY OF THE INVENTION

Thus, in accordance with the present invention, there are provided methods of treatment, prevention and/or diagnosis related to identifying patient's genotype at position +316 of at least one ODC1 promoter gene allele.

In one aspects, there is provided a method for the preventative or curative treatment of carcinoma in a patient comprising:

a) obtaining results from a test that determines the patient's genotype at position +316 of at least one ODC1 promoter gene allele; and b) if the results indicate that the patient's genotype at position +316 of at least one allele of the ODC1 promoter gene is G, administering to the patient effective amounts of a pharmaceutical therapy comprising:
  (i) a first agent that inhibits ornithine decarboxylase (ODC) within the patient; and
  (ii) a second agent that modulates the polyamine pathway to reduce overall polyamine content within the patient when combined with the first agent.

In some embodiments, the second agent also increases the expression of sperm-idine/spermine $N^1$-acetyltransferase within the patient. In some embodiments, the results are obtained by receiving a report containing said genotype or taking a patient history that reveals the results. In some embodiments, the test determines the nucleotide base at position +316 of one allele of the ODC1 promoter gene of the patient. In some embodiments, the test determines the nucleotide bases at position +316 of both alleles of the ODC1 promoter gene of the patient. In some embodiments, the results indicate that the patient's genotype at position +316 of both alleles of the ODC1 promoter gene is GG. In some embodiments, the results indicate that the patient's genotype at position +316 of both alleles of the ODC1 promoter gene is GA.

In some embodiments, the pharmaceutical therapy further comprises increasing the dosage of the first or the second agent if the patient was already being treated with the pharmaceutical therapy, but at a lower dosage, prior to obtaining to the results of the test. In some embodiments, the pharmaceutical therapy further comprises increasing the dosage of the first and the second agent if the patient was already being treated with the pharmaceutical therapy, but at a lower dosage, prior to obtaining to the results of the test. In some embodiments, the first agent is α-difluoromethylornithine (DFMO). In some embodiments, the second agent is a non-aspirin containing non-steroidal anti-inflammatory drug (NSAID). In some embodiments, the non-aspirin containing NSAID is a selective COX-2 inhibitor. In some embodiments, the non-aspirin containing NSAID is sulindac or celecoxib. In some embodiments, the non-aspirin containing NSAID is sulindac.

In another aspect, there is provided a method for the treatment of colorectal carcinoma risk factors in a patient comprising:

a) obtaining results from a test that determines the patient's genotype at position +316 of at least one ODC1 promoter gene allele; and b) if the results indicate that the patient's genotype at position +316 of at least one allele of the ODC1 promoter gene is G, administering to the patient effective amounts of a pharmaceutical therapy comprising:

(i) a first agent that inhibits ornithine decarboxylase (ODC) within the patient; and (ii) a second agent that modulates the polyamine pathway to reduce overall polyamine content within the patient when combined with the first agent, wherein the method prevents the formation of new aberrant crypt foci, new adenomatous polyps or new adenomas with displasia in the patient.

In some embodiments, the second agent also increases the expression of spermidine/spermine $N^1$-acetyltransferase within the patient. In some embodiments, the method prevents the formation of new aberrant crypt foci in the patient. In some embodiments, the method prevents the formation of new adenomatous polyps in the patient. In some embodiments, the method prevents the formation of new adenomas with displasia in the patient. In some embodiments, the results are obtained by receiving a report containing said genotype or taking a patient history that reveals the results. In some embodiments, the test determines the nucleotide base at position +316 of one allele of the ODC1 promoter gene of the patient. In some embodiments, the test determines the nucleotide bases at position +316 of both alleles of the ODC1 promoter gene of the patient. In some embodiments, the results indicate that the patient's genotype at position +316 of both alleles of the ODC1 promoter gene is GG. In some embodiments, the results indicate that the patient's genotype at position +316 of both alleles of the ODC1 promoter gene is GA.

In some embodiments, the pharmaceutical therapy further comprises increasing the dosage of the first or the second agent if the patient was already being treated with the pharmaceutical therapy, but at a lower dosage, prior to obtaining to the results of the test. In some embodiments, the pharmaceutical therapy further comprises increasing the dosage of the first and the second agent if the patient was already being treated with the pharmaceutical therapy, but at a lower dosage, prior to obtaining to the results of the test. In some embodiments, the first agent is α-difluoromethylornithine (DFMO). In some embodiments, the second agent is a non-aspirin containing non-steroidal anti-inflammatory drug (NSAID). In some embodiments, the non-aspirin containing NSAID is a selective COX-2 inhibitor. In some embodiments, the non-aspirin containing NSAID is sulindac or celecoxib. In some embodiments, the non-aspirin containing NSAID is sulindac.

In another aspect, there is provided a method for evaluating the suitability of a patient for preventative or curative treatment of carcinoma, comprising:

a) obtaining results from a test that determines the patient's genotype at position +316 of at least one ODC1 promoter gene allele; and b) if the results indicate that the patient's genotype at position +316 of at least one allele of the ODC1 promoter gene is G, identifying the patient as suitable for treatment by a pharmaceutical therapy, said therapy comprising combined effective amounts of a first agent that inhibits ornithine decarboxylase (ODC) within the patient; and a second agent that modulates the polyamine pathway to reduce overall polyamine content within the patient when combined with the first agent.

In some embodiments, the second agent also increases the expression of sperm-idine/spermine $N^1$-acetyltransferase within the patient. In some embodiments, the results are obtained by receiving a report containing said genotype or taking a patient history that reveals the results. In some embodiments, the test determines the nucleotide base at position +316 of one allele of the ODC1 promoter gene of the patient. In some embodiments, the test determines the nucleotide bases at position +316 of both alleles of the ODC1 promoter gene of the patient. In some embodiments, the results indicate that the patient's genotype at position +316 of both alleles of the ODC1 promoter gene is GG. In some embodiments, the results indicate that the patient's genotype at position +316 of both alleles of the ODC1 promoter gene is GA. In some embodiments, the pharmaceutical therapy further comprises increasing the dosage of the first or the second agent if the patient was already being treated with the pharmaceutical therapy, but at a lower dosage, prior to obtaining to the results of the test. In some embodiments, the pharmaceutical therapy further comprises increasing the dosage of the first and the second agent if the patient was already being treated with the pharmaceutical therapy, but at a lower dosage, prior to obtaining to the results of the test. In some embodiments, the first agent is α-difluoromethylornithine (DFMO). In some embodiments, the second agent is a non-aspirin containing non-steroidal anti-inflammatory drug (NSAID). In some embodiments, the non-aspirin containing NSAID is a selective COX-2 inhibitor. In some embodiments, the non-aspirin containing NSAID is sulindac or celecoxib. In some embodiments, the non-aspirin containing NSAID is sulindac.

In another aspect, there is provided a method of rendering a carcinoma tumor in a patient resectable comprising:

a) obtaining results from a test that determines the patient's genotype at position +316 of at least one ODC1 promoter gene allele; and b) if the results indicate that the patient's genotype at position +316 of at least one allele of the ODC1 promoter gene is G, administering to the patient effective amounts of a pharmaceutical therapy comprising:

(i) a first agent that inhibits ornithine decarboxylase (ODC) within the patient; and (ii) a second agent that increases the expression of sperm-idine/spermine $N^1$-acetyltransferase within the patient.

In some embodiments, the results are obtained by receiving a report containing said genotype or taking a patient history that reveals the results. In some embodiments, the test determines the nucleotide base at position +316 of one allele of the ODC1 promoter gene of the patient. In some embodiments, the test determines the nucleotide bases at position +316 of both alleles of the ODC1 promoter gene of the patient. In some embodiments, the results indicate that the patient's genotype at position +316 of both alleles of the ODC1 promoter gene is GG. In some embodiments, the results indicate that the patient's genotype at position +316 of both alleles of the ODC1 promoter gene is GA.

In some embodiments, the pharmaceutical therapy further comprises increasing the dosage of the first or the second agent if the patient was already being treated with the pharmaceutical therapy, but at a lower dosage, prior to obtaining to the results of the test. In some embodiments, the pharmaceutical therapy further comprises increasing the dosage of the first and the second agent if the patient was already being treated with the pharmaceutical therapy, but at a lower dosage, prior to obtaining to the results of the test. In some embodiments, the first agent is α-difluoromethylornithine (DFMO).

In some embodiments, the second agent is a non-aspirin containing non-steroidal anti-inflammatory drug (NSAID). In some embodiments, the non-aspirin containing NSAID is a selective COX-2 inhibitor. In some embodiments, the non-aspirin containing NSAID is sulindac or celecoxib. In some embodiments, the non-aspirin containing NSAID is sulindac.

In another aspect, there is provided a method for preventing the development or recurrence of a carcinoma in a patient at risk therefor comprising:
   a) obtaining results from a test that determines the patient's genotype at position +316 of at least one ODC1 promoter gene allele; and
   b) administering to the patient combined effective amounts of α-difluoromethylornithine (DFMO) and a non-aspirin containing non-steroidal anti-inflammatory drug (NSAID) if the results indicate that the patient's genotype at position +316 of at least one allele of the ODC1 promoter gene is G.

In some embodiments, the results are obtained by receiving a report containing said genotype or taking a patient history that reveals the results. In some embodiments, the test determines the nucleotide base at position +316 of one allele of the ODC1 promoter gene of the patient. In some embodiments, the test determines the nucleotide bases at position +316 of both alleles of the ODC1 promoter gene of the patient. In some embodiments, the results indicate that the patient's genotype at position +316 of both alleles of the ODC1 promoter gene is GG. In some embodiments, the results indicate that the patient's genotype at position +316 of both alleles of the ODC1 promoter gene is GA.

In another aspect, there is provided a method for treating a patient at risk for development or recurrence of carcinoma with α-difluoromethylornithine (DFMO) and a non-aspirin containing non-steroidal anti-inflammatory drug (NSAID), comprising administering to the patient effective amounts of α-difluoromethylornithine (DFMO) and a non-aspirin containing non-steroidal anti-inflammatory drug (NSAID), wherein the patient has been identified as having a G at position +316 of at least one ODC1 promoter gene allele.

In some embodiments, the genotype identified at position +316 of both of the patient's ODC1 promoter gene alleles is GG. In some embodiments, the genotype identified at position +316 of both of the patient's ODC1 promoter gene alleles is GA.

In another aspect, there is provided a method for treating a carcinoma in a patient comprising:
   a) obtaining results from a test that determines the patient's genotype at position +316 of at least one ODC1 promoter gene allele; and
   b) administering to the patient combined effective amounts of α-difluoromethylornithine (DFMO) and a non-aspirin containing non-steroidal anti-inflammatory drug (NSAID) if the results indicate that the patient's genotype at position +316 of the ODC1 promoter gene of at least one allele is G.

In some embodiments, the results are obtained by receiving a report containing said genotype or taking a patient history that reveals the results. In some embodiments, the test determines the nucleotide base at position +316 of one allele of the ODC1 promoter gene of the patient. In some embodiments, the test determines the nucleotide bases at position +316 of both alleles of the ODC1 promoter gene of the patient. In some embodiments, the results indicate that the patient's genotype at position +316 of both alleles of the ODC1 promoter gene is GG. In some embodiments, the results indicate that the patient's genotype at position +316 of both alleles of the ODC1 promoter gene is GA.

In variations on any of the above embodiments, the non-aspirin containing NSAID is a selective COX-2 inhibitor. In some embodiments, the non-aspirin containing NSAID is sulindac or celecoxib. In some embodiments, the non-aspirin containing NSAID is sulindac. In some embodiments, DFMO and sulindac are administered systemically. In some embodiments, DFMO and sulindac are administered by distinct routes. In some embodiments, the DFMO or the non-aspirin containing NSAID is administered orally, intraarterially or intravenously. In some embodiments, the DFMO is administered orally. In some embodiments, the effective amount of DFMO is 500 mg/day. In some embodiments, the DFMO is administered intravenously. In some embodiments, the effective amount of DFMO is from about 0.05 to about 5.0 $g/m^2/day$. In some embodiments, the DFMO and the non-aspirin containing NSAID is formulated for oral administration. In some embodiments, the DFMO and the non-aspirin containing NSAID is formulated as a hard or soft capsule or a tablet. In some embodiments, the DFMO and the non-aspirin containing NSAID is administered every 12 hours. In some embodiments, the DFMO and the non-aspirin containing NSAID is administered every 24 hours. In some embodiments, the effective amount of sulindac is from about 10 to about 1500 mg/day. In some embodiments, the effective amount of sulindac is from about 10 to about 400 mg/day. In some embodiments, the effective amount of sulindac is 150 mg/day. In some embodiments, DFMO is administered prior to sulindac. In some embodiments, DFMO is administered after sulindac. In some embodiments, DFMO is administered before and after sulindac. In some embodiments, DFMO is administered concurrently with sulindac. In some embodiments, DFMO is administered at least a second time. In some embodiments, sulindac is administered at least a second time.

In variations on any of the above embodiments, the patient has a solid tumor, and said method further comprises resection of said solid tumor. In some embodiments, DFMO and sulindac are administered prior to said resection. In some embodiments, DFMO and sulindac are administered after said resection.

In variations on any of the above embodiments, the carcinoma is colorectal cancer, breast cancer, pancreatic cancer, brain cancer, lung cancer, stomach cancer, a blood cancer, skin cancer, testicular cancer, prostate cancer, ovarian cancer, liver cancer or esophageal cancer, cervical cancer, head and neck cancer, non-melanoma skin cancer, neuroblastoma and glioblastoma. In some embodiments, the carcinoma is colorectal cancer. In some embodiments, the colorectal cancer is stage I. In some embodiments, the colorectal cancer is stage II. In some embodiments, the colorectal cancer is stage III. In some embodiments, the colorectal cancer is stage IV.

In variations on any of the above embodiments, the method prevents the formation of new advanced colorectal neoplasms within the patient. In some embodiments, the method prevents ototoxicity or the risk thereof within the patient. In some embodiments, the method prevents the formation of new right-sided advanced colorectal neoplasms. In some embodiments, the method prevents the formation of new left-sided advanced colorectal neoplasms.

In variations on any of the above embodiments, the patient has been identified as having one or more adenomatous polyps in the colon, rectum or appendix. In some embodiments, the patient has been identified as having one or more advanced colorectal neoplasms. In some embodiments, the patient has been identified as having one or more left-side advanced colorectal neoplasms. In some embodiments, the patient has been identified as having one or more right-sided advanced colorectal neoplasms. In some embodiments, the patient has been diagnosed with familial adenomatous polyposis. In some embodiments, the patient has been diagnosed with Lynch syndrome. In some embodiments, the patient has been diagnosed with familial colorectal cancer type X. In some embodiments, the patient satisfies the Amsterdam Criteria or the Amsterdam Criteria II. In some embodiments, the patient has a history of resection of one or more colorectal adenomas. In some embodiments, the patient has an intraepithelial neoplasia or a precancerous lesion associated ODC hyperactivity. In some embodiments, the patient has an intraepithelial neoplasia or a precancerous lesion and elevated cellular polyamine levels.

In variations on any of the above embodiments, the patient is human.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result.

As used herein, the term "$IC_{50}$" refers to an inhibitory dose which is 50% of the maximum response obtained.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

"Effective amount," "Therapeutically effective amount" or "pharmaceutically effective amount" means that amount which, when administered to a subject or patient for treating a disease, is sufficient to effect such treatment for the disease.

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any of the reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

Other objects, features and advantages of the present disclosure will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description. Note that simply because a particular compound is ascribed to one particular generic formula doesn't mean that it cannot also belong to another generic formula.

BRIEF DESCRIPTION OF THE DRAWINGS

The following drawings form part of the present specification and are included to further demonstrate certain aspects of the present disclosure. The invention may be better understood by reference to one of these drawings in combination with the detailed description of specific embodiments presented herein.

FIG. 4A shows E-box protein expression in colon-derived cells. Expression of proteins to be evaluated for binding to the +316 ODC1 SNP was assessed by Western blot analysis. Extracts of both HT29 and HCT116 cells were evaluated for c-MYC, MAD1, and MAD4; β-actin was used as a loading control.

FIG. 5A shows the effect of c-MYC expression on ODC1 allele-specific promoter activity in HT29 colon-derived cells. Promoter activity was measured after transfection with ODC1 promoter reporter plasmids co-transfected with pcDNA 3.0 plasmid or CMV-MYC expression vector. Promoter constructs differ by the presence of the first E-box element, located in −485 to −480 by ("wt E-box1" for the wild-type sequence or "mut E-box1" for a mutant sequence). The constructs differ also by the ODC1 +316 SNP ("+316 G" or "+316 A"). *, $P \leq 0.013$ for each of the four comparisons relative to promoter activity with pcDNA 3.0 cotransfection.

DESCRIPTION OF ILLUSTRATIVE EMBODIMENTS

Figure 1:
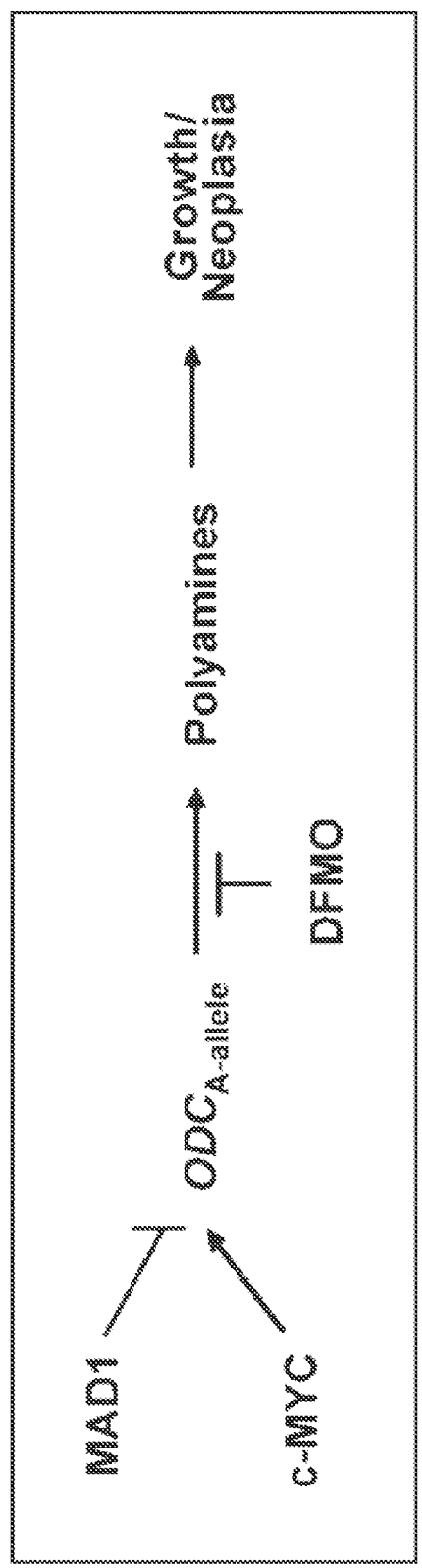
FIG. 1—Differential Effects of Polyamine Regulation by MAD1 and c-MYC. Schema depicting the proposed differential effects of polyamine regulation by MAD1 and c-MYC on the ODC1 +316 minor A-allele. Effects of the ODC inhibitor DFMO (difluoromethylornithine) are also shown.

In several aspects, methods are provided that comprise predicting the suitability, efficacy, toxicity and/or dosage of anti-carcinoma combination therapies comprising ornithine decarboxylase (ODC) inhibitor and a spermidine/spermine $N^1$-acetyltransferase expression agonist based at least in part on the patient's ODC1 promoter genotype.

The present invention also involves the delivery of therapeutic compounds to individuals exhibiting pre-cancerous symptoms to prevent the onset of cancer and/or to prevent the onset of cancer risk factors, such as the formation of new aberrant crypt foci, the formation of new adenomatous polyps or new adenomas with dysplasia. Cells of this category include polyps and other precancerous lesions, premalignancies, preneoplastic or other aberrant phenotype indicating probable progression to a cancerous state, based at least in part on the patient's ODC1 promoter genotype.

I. Polyamines Metabolism

Excess polyamine formation has long been implicated in epithelial carcinogenesis, particularly colorectal carcinogenesis. Polyamines are small ubiquitous molecules involved in various processes, including transcription, RNA stabilization, ion channel gating and others (Wallace, 2000). Ornithine decarboxylase (ODC), the first enzyme in polyamine synthesis, is essential for normal development and tissue repair in mammals but is down-regulated in most adult tissues (Gerner and Meyskens, 2004). Multiple abnormalities in the control of polyamine metabolism and transport result in increased polyamine levels that can promote tumorigenesis in several tissues (Thomas and Thomas, 2003).

Polyamine metabolism is up-regulated in intestinal epithelial tissues of humans with familial adenomatous polyposis (FAP) (Giardiello et al., 1997), a syndrome associated with high risk of colon and other cancers.

FAP may be caused by mutations in the adenomatous polyposis coli (APC) tumor suppressor gene, and APC signaling has been shown regulates ODC expression in both human cells (Fultz and Gerner, 2002) and in a mouse model of FAP (Erdman et al., 1999).

Wild type APC expression leads to decreased expression of ODC, while mutant APC leads to increased expression of ODC. The mechanism of APC-dependent regulation of ODC involves E-box transcription factors, including the transcriptional activator c-MYC and the transcriptional repressor MAD1 (Fultz and Gerner, 2002; Martinez et al., 2003). c-MYC was shown by others to regulate ODC transcription (Bellofernandez et al., 1993). Several genes involved in polyamine metabolism are essential genes for optimal growth in most organisms, and are down-regulated in non-proliferating and/or adult cells and tissues (Gerner and Meyskens, 2004). The polyamines influence specific cellular phenotypes, in part, by affecting patterns of gene expression, as reviewed elsewhere (Childs et al., 2003).

As described below, a strategy involving inhibition of ODC activity (i.e., the rate-limiting enzyme of polyamine synthesis) and/or reduction of cellular polyamine levels has demonstrated remarkable efficacy in preventing recurrence of colorectal polyps in humans. Epidemiologic and experimental results from the present research demonstrate conditional regulation of polyamine homeostasis by genetic polymorphism in ODC, and suggest a model in which the +316 ODC SNP may be protective for colon adenoma recurrence and detrimental for survival after colon cancer diagnosis. This information may be used for determining colon cancer prognosis. By identifying patients at increased risk for cancer progression/recurrence, early implementation of tertiary prevention management strategies can be instituted. Additionally, this research may be used to identify high-risk but otherwise optimally-treated locoregional colorectal cancer patients that would benefit from tertiary cancer prevention therapies.

Depending on a patient's diet, the excess polyamine problem may be compounded by the fact that polyamines, e.g., putrescine is present in many common foods, such as orange juice, which contains approximately 400 ppm putrescine. In this regard, a high polyamine diet is contraindicatory, and for some of the embodiments provided herein such a diet is to be avoided. See U.S. Provisional Patent Application by Kavitha P. Raj, Jason A. Zell, Christine E. McLaren, Eugene W. Gerner, Frank L. Meyskens and Jeffrey Jacob, entitled "Cancer Prevention and Treatment Methods Based on Dietary Polyamine Content," filed May 14, 2010, which is incorporated by reference in its entirety.

II. Familial Adenomatous Polyposis

Familial Adenomatous Polyposis (FAP), an inherited polyposis syndrome, is the result of germ-line mutation of the adenomatous polyposis coli (APC) tumor suppressor gene (Su et al., 1992). This autosomal-dominant condition with variable expression is associated with the development of hundreds of colonic adenomas, which uniformly progress to adenocarcinoma by forty years of age, two decades earlier than the mean age diagnosis for sporadic colon cancer (Bussey, 1990). In prior studies of pre-symptomatic individuals with FAP, increased levels of the polyamines spermidine and spermine, and their diamine precursor putrescine, have been detected in normal-appearing colorectal biopsies when compared to normal family member controls (Giardiello et al., 1997). The activity of ornithine decarboxylase (ODC), the first and rate-limiting enzyme in mammalian polyamine synthesis, also is elevated in apparently normal colonic mucosal biopsies from FAP patients (Giardiello et al., 1997; Luk and Baylin, 1984). These findings are of interest as the polyamines are necessary for optimal cell proliferation (Pegg, 1986). Further, suppression of ODC activity, using the enzyme-activated irreversible inhibitor DFMO, inhibits colon carcinogenesis in carcinogen-treated rodents (Kingsnorth et al., 1983; Tempero et al., 1989).

Figure 9:
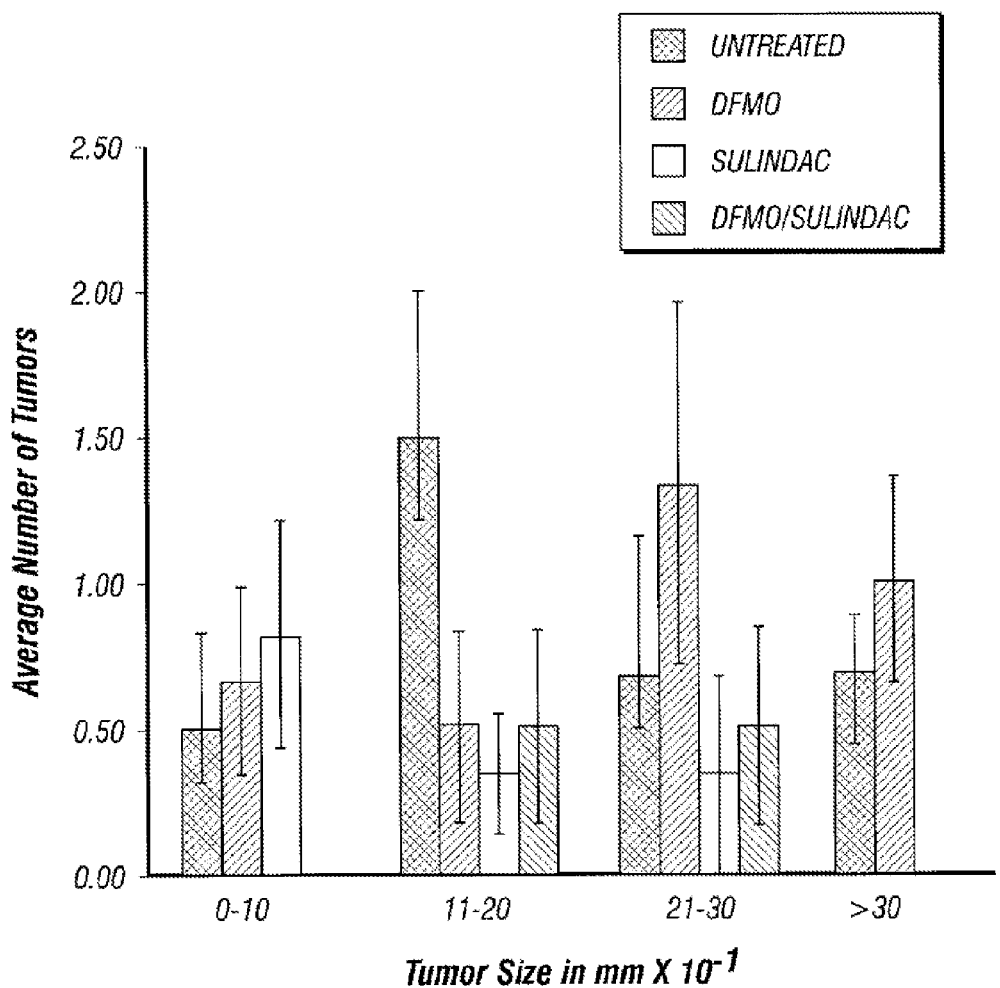
FIG. 9—Average Number of Tumors by Size in Colon of Min/+ Mice. This figure shows the average number of tumors by size in the colon of the three treatment groups compared to untreated controls. Mice, purchased from The Jackson Laboratory (Bar Harbor, Me.), were bred crossing C57BL/6J-Apc$^{Min/+}$ males and C57/BL6 females. Heterozygous Min mice (Apc$^{Min}$/Apc$^+$): (heterozygous for a nonsense mutation at codon 850 of Apc) were identified by genotyping at weaning by an allele specific PCR assay using tail-tip DNA. Homozygous (Apc$^+$/Apc$^+$) litter mates served as controls. One treatment consisted of supplementing drinking water with 2% DFMO (Merrell Dow Research Inst.) on the 8th day of study. In the other treatment, 167 ppm of sulindac (Harlen Teklad) was added to AIN-93G mouse diet on the 21st day of the study. The third treatment was a combination of DFMO and sulindac. After 114 days, the mice were sacrificed through $CO_2$ asphyxiation. The small intestine and colon segments were removed from mice and dissected lengthwise, mounted and fixed in 70% ethanol, and placed at 4° C. for tumor scoring. Representative tissues were also taken for histopathology evaluation.
Figure 10:
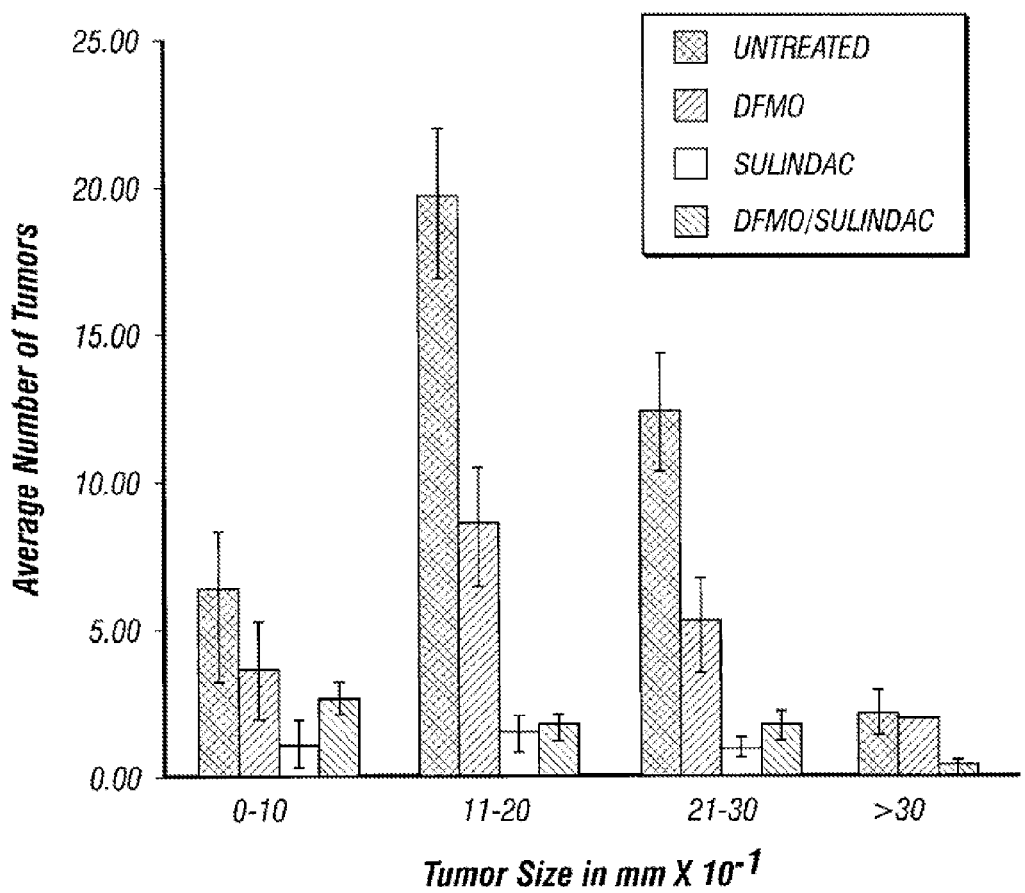
FIG. 10—Average Number of Tumors by Size in the Small Intestine of Min/+ Mice. This figure shows the average number of tumors by size in the small intestine of the three treatment groups compared to untreated controls. For experimental details, see FIG. 9 description above.
Figure 11:
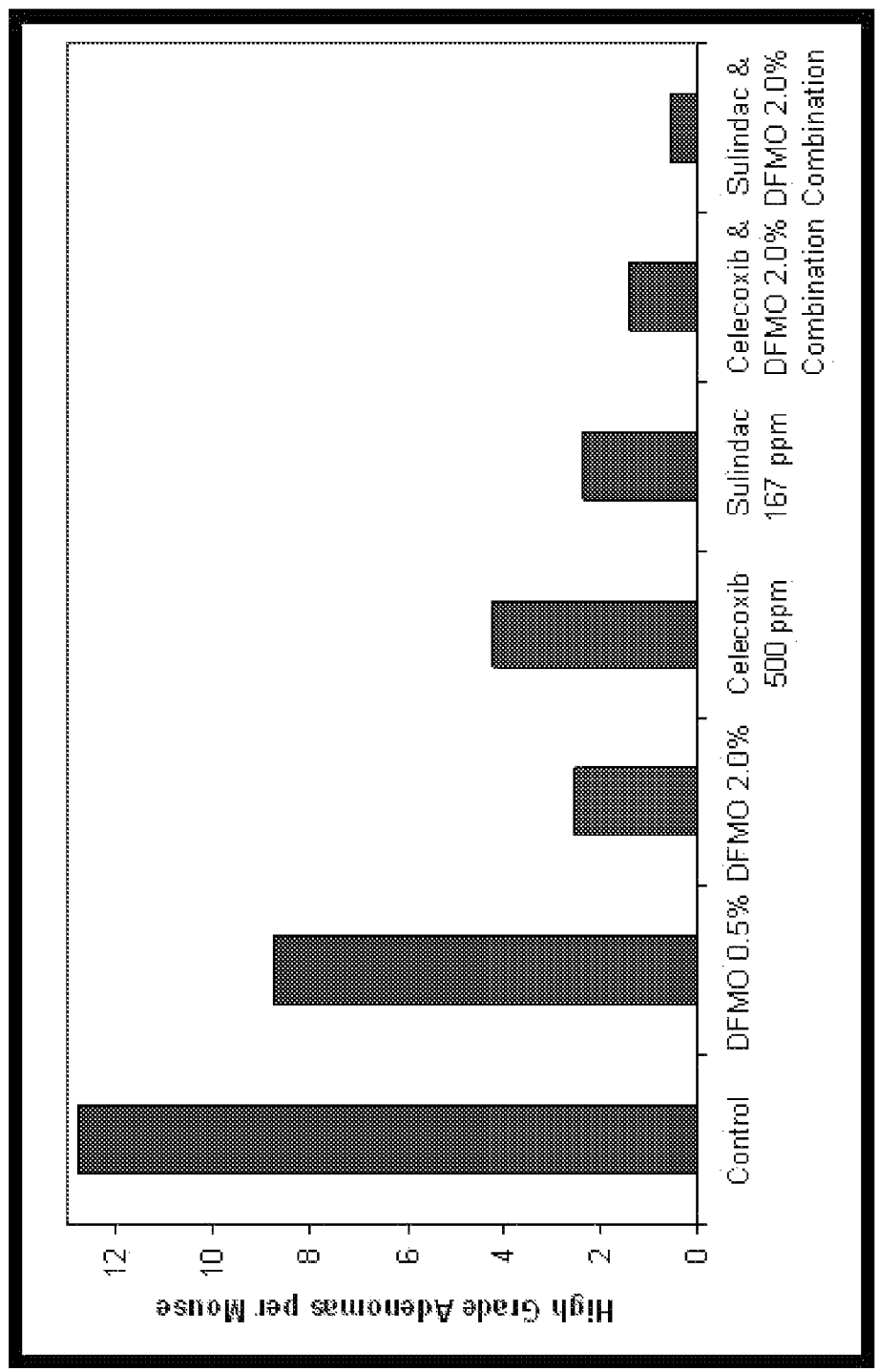
FIG. 11—Number of High Grade Adenomas as a Function of Therapy in Min/+ Mice. This figure shows how the number of high grade adenomas various depending on therapy type. For experimental details, see FIG. 9 description above.

As discussed in greater detail below, the Min (multiple intestinal neoplasia) mouse, which shares a mutated APC/apc genotype with FAP, serves as a useful experimental animal model for human FAP patients (Lipkin, 1997). The Min mouse can develop greater than 100 gastrointestinal adenomas/adenocarcinomas throughout the gastrointestinal tract by 120 days of life leading to GI bleeding, obstruction and death. A combination therapy of DFMO and sulindac was shown to be effective in reducing adenomas in these mice (U.S. Pat. No. 6,258,845; Gerner and Meyskens, 2004). The results of treating Min mice with either DFMO alone, sulindac alone, or a combination of DFMO and sulindac on tumor formation in either the colon or small intestine are shown in FIGS. 9-11.

III. Ornithine Decarboxylase-1 Polymorphism

Activity of ornithine decarboxylase (ODC), the first enzyme in polyamine synthesis, is required for normal growth and is elevated in many cancers, including colorectal cancer. Herein associations of the +316 ODC single nucleotide polymorphism (SNP) with colorectal cancer (CRC)-specific survival among CRC cases were examined and its functional significance in colon cancer cells was investigated.

A single nucleotide polymorphism (SNP) in intron-1 of the human ODC1 gene affects ODC1 transcription (Guo et al., 2000), and has been investigated as a genetic marker for colorectal adenoma (CRA) risk (Martinez et al., 2003; Barry et al., 2006; Hubner et al., 2008). The reported minor A-allele frequency is approximately 25% and despite differences across race/ethnicity, ODC1 genotype distribution is in Hardy-Weinberg equilibrium within each race (O'Brien et al., 2004; Zell et al., 2009). Individuals homozygous for the ODC1 minor A-allele have reduced risk of adenoma recurrence compared to those with the major G-allele (Martinez et al., 2003; Hubner et al., 2008). Furthermore, the ODC1 A-allele (AA or GA genotype, but not GG genotype) and reported aspirin usage have been associated with reduced colon polyp recurrence (Martinez et al., 2003; Barry et al., 2006; Hubner et al., 2008), and a statistically significant 50% reduced risk of advanced adenomas (Barry et al., 2006).

Figure 2:
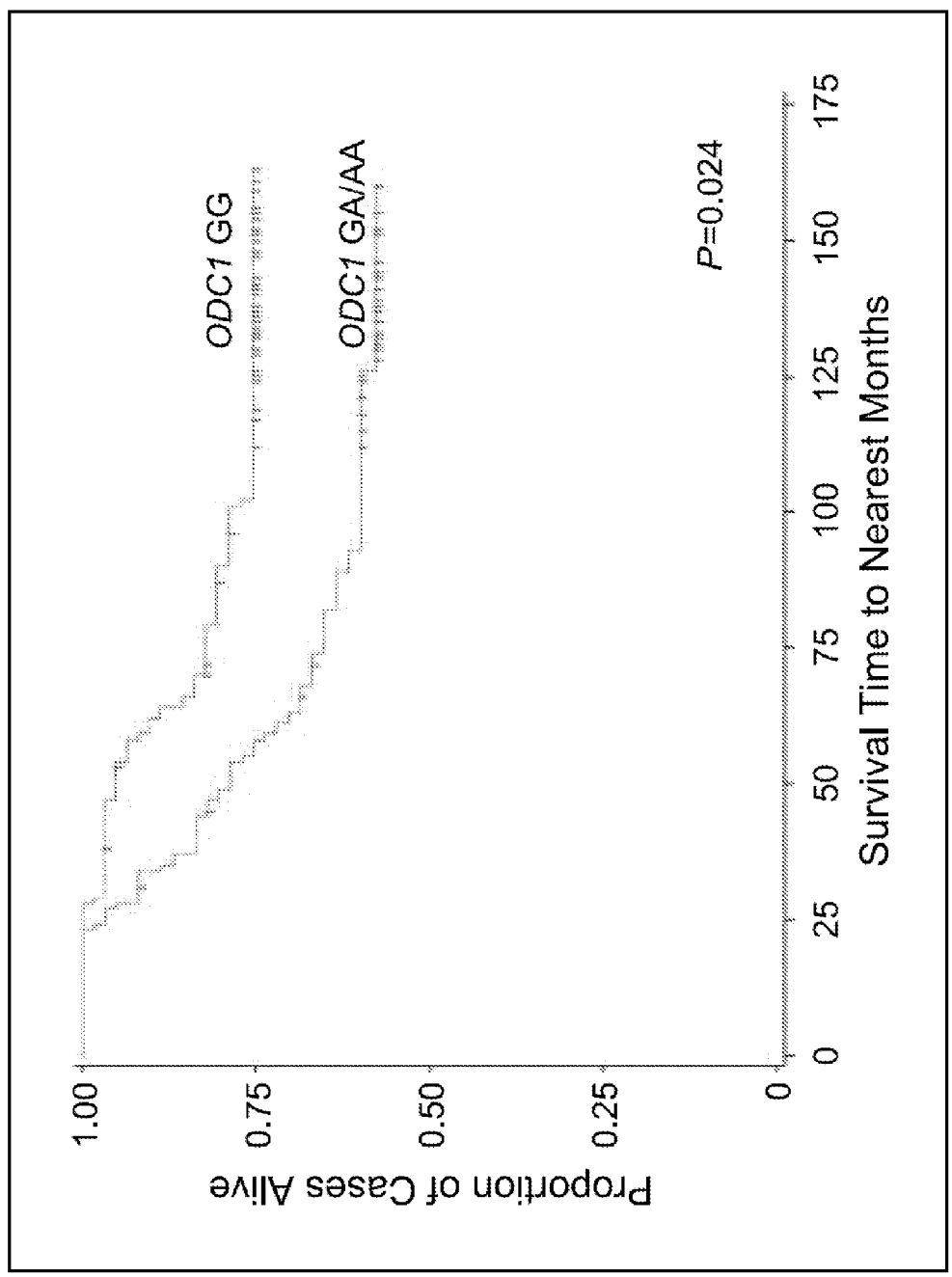
FIG. 2—Colorectal Cancer-Specific Survival Rate Estimates. This figure shows Kaplan-Meier colorectal cancer-specific survival rate estimates for cases with stage III colorectal cancer, stratified by ODC1 +316 genotype. Included are cases from the University of California Irvine Gene-Environment Study of Familial Colorectal Cancer diagnosed during the period 1994-1996 with follow-up through March 2008: ODC1 GG (64 cases, 15 colorectal cancer-specific deaths), ODC1 GA/AA (62 cases, 25 colorectal cancer-specific deaths).

The ODC allele-specific binding of E-box transcription factors was investigated and the functional significance of the +316 ODC SNP, located between two E-boxes was evaluated (E-box 2 and 3 as depicted in FIG. 2A). Each cell line genotype influences a consensus PstI restriction site in this region. FIG. 2B shows that a polymerase chain reaction (PCR) product made from human colon HT29 cells was partially sensitive to PstI cutting, suggesting that these cells contained at least one ODC A-allele. A PCR product made from human colon HCT116 cells using the same primers was insensitive to PstI action, implying that these cells contained only ODC G-alleles. This result was confirmed by direct DNA sequencing.

Figure 3:
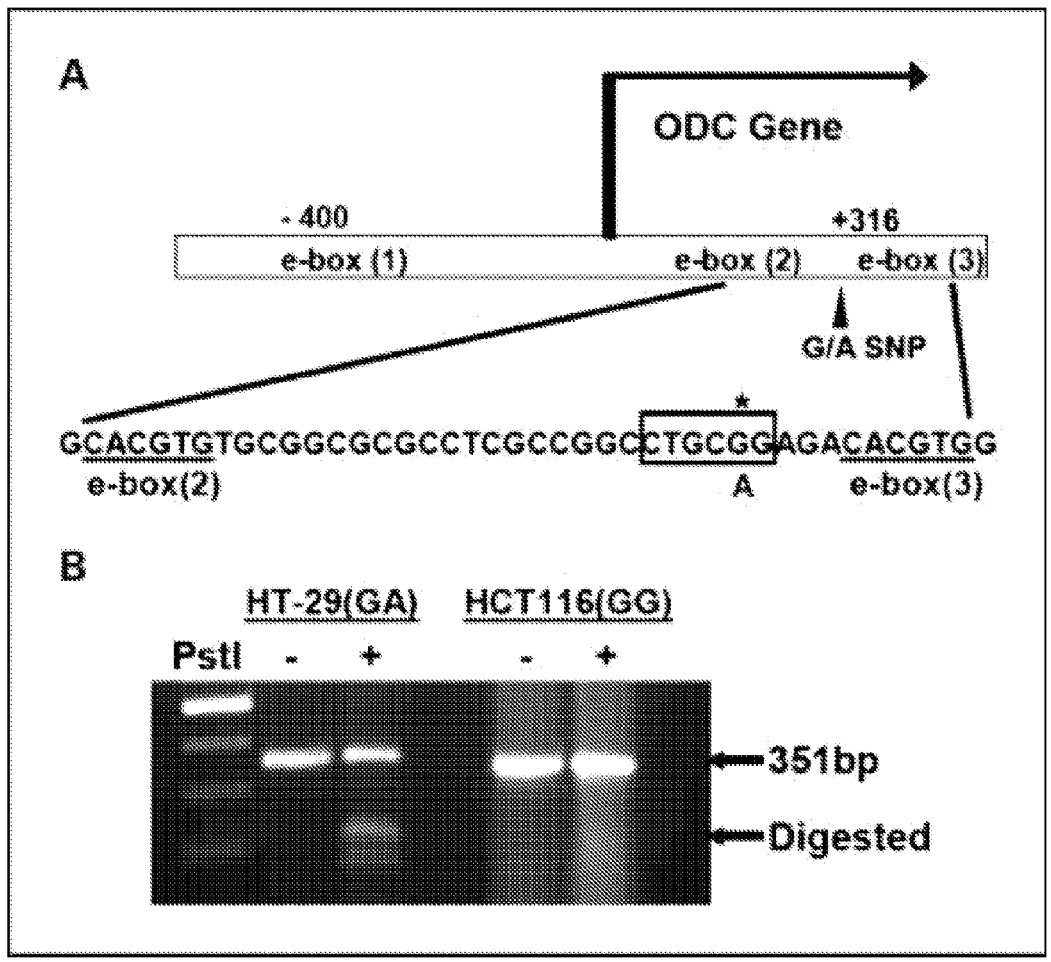
FIGS. 3A & B—Location and Analysis of the ODC1 promoter SNP. FIG. A shows the A, location of the ODC1 promoter SNP. The SNP under investigation in this study is 316 nucleotides 3' of the ODC1 transcription start site (*). This SNP resides between two consensus E-boxes as shown by the underlined sequences, and affects a PstI restriction site (box) (SEQ ID NO:5).
FIG. 3B shows a restriction fragment length polymorphism analysis of ODC1 SNP. The DNA was obtained from two cell types, and the region surrounding the ODC1 SNP site was sequenced. Colon-derived HT29 cells were found to be heterozygous GA, whereas HCT116 cells were found to be homozygous GG, at the ODC1 SNP locus. A 350-bp PCR product of this region was obtained from each cell type and subjected to digestion with PstI. Evidence of an A-allele was indicated by restriction products <350 bp.

Expression of specific E-box binding proteins, including the transcriptional activator c-MYC and several transcriptional repressors in HT29 and HCT116 cells (e.g. MAD1 and MAD4), was established by Western blotting (FIG. 3A). Chromatin immunoprecipitation (CHIP) analysis of the region surrounding +316 of the ODC promoter was conducted, using antibodies directed against these proteins. As shown in FIG. 3B, ODC promoter-specific PCR products were synthesized from HT29 DNA obtained after immunoprecipitation of chromatin with antibodies directed against c-MYC, MAD1 or MAD4. PCR products synthesized from HCT116 DNA after similar chromatin immunoprecipitation were substantially reduced compared to those synthesized from HT29 DNA. Quantification of these results indicated that c-MYC, MAD1, and MAD4 binding to the ODC SNP region was 4-14 times greater in HT29 cells, which contained one ODC-A allele, compared to HCT116 cells, which contained only ODC-G alleles.

Figure 4:
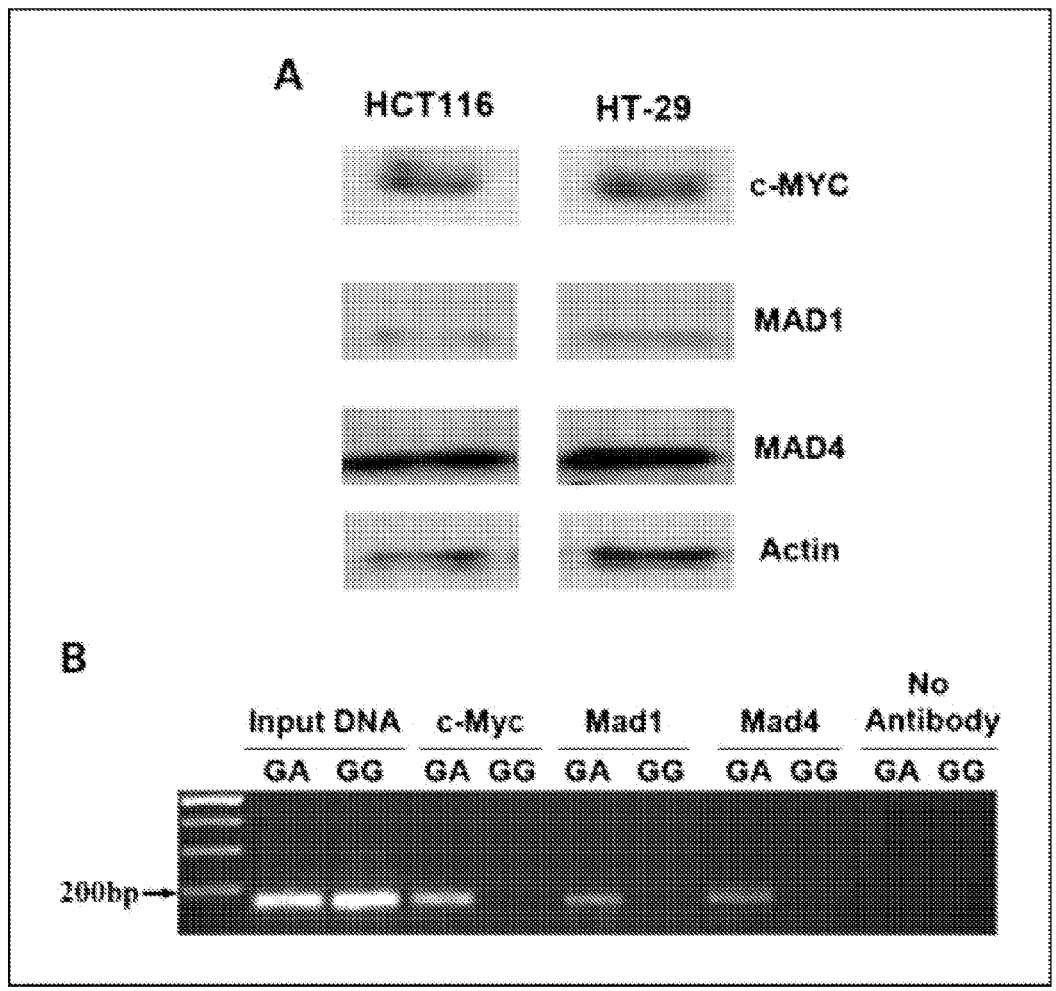
FIGS. 4A & B—E-Box Expression and Immunoprecipitation Analysis. Location of the ODC1 promoter SNP.
FIG. 4B shows documentation for the allele-specific transcription factor binding by chromatin immunoprecipitation analysis, which was conducted as described in the examples section below. HT29 cells were a source of ODC1 A-alleles, as these cells are heterozygous GA at this site. HCT116 cells were used as a source of ODC1 G-alleles.
Figure 5:
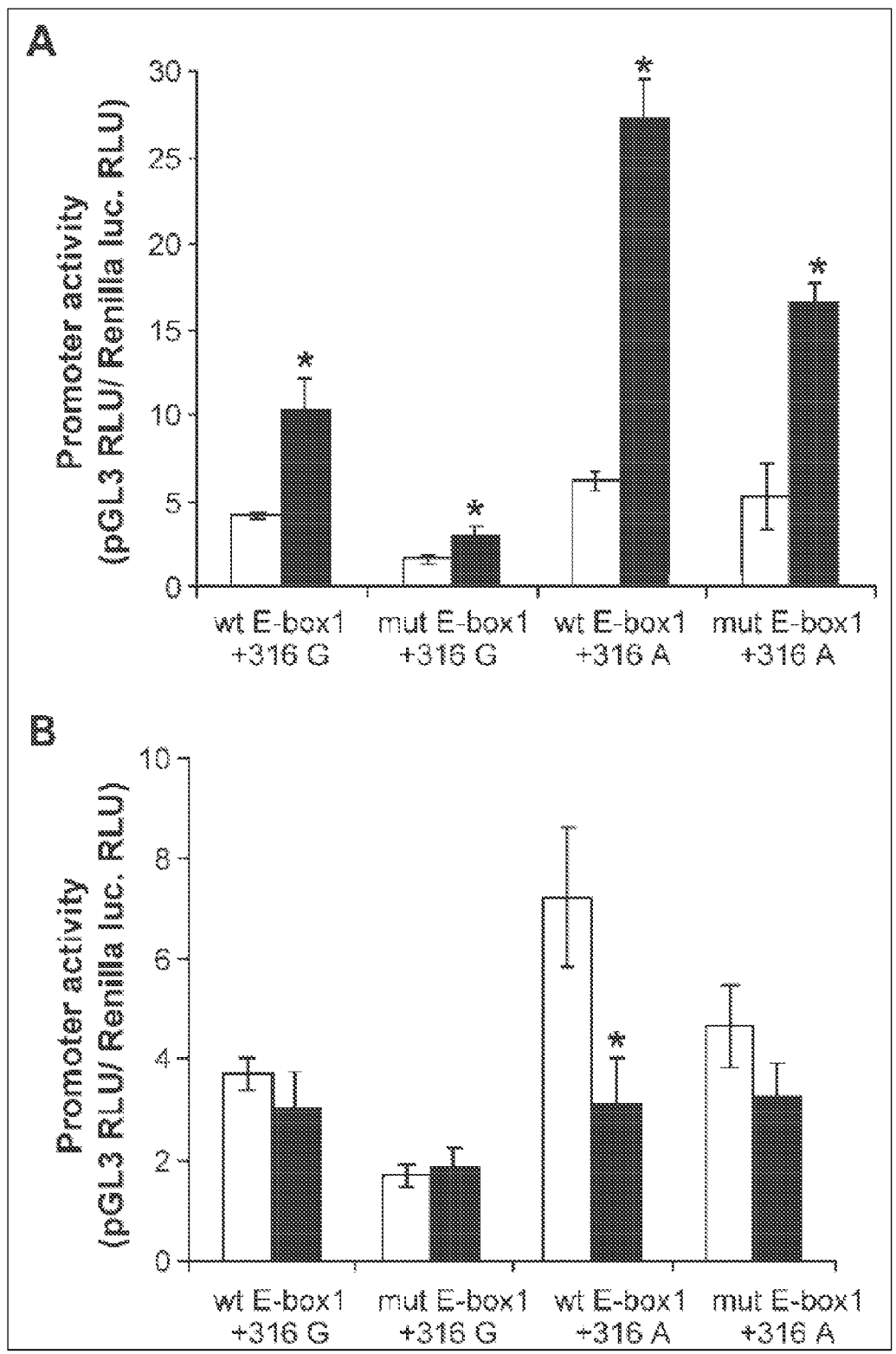
FIGS. 5A & B—Effects of c-MYC and MAD1 expression on ODC1 Activity.
FIG. 5B shows the effect of MAD1 expression on ODC1 allele-specific promoter activity in HT29 colon tumor derived cells. Promoter activity was measured after transfection with ODC1 promoter reporter plasmids cotransfected with pcDNA 3.1 plasmid or with a pcDNA-MAD1 plasmid. Promoter constructs used were described in the legend for panel A of this figure. *, P=0.027, statistical significance relative to promoter activity with pcDNA 3.1 cotransfection.
Figure 6:
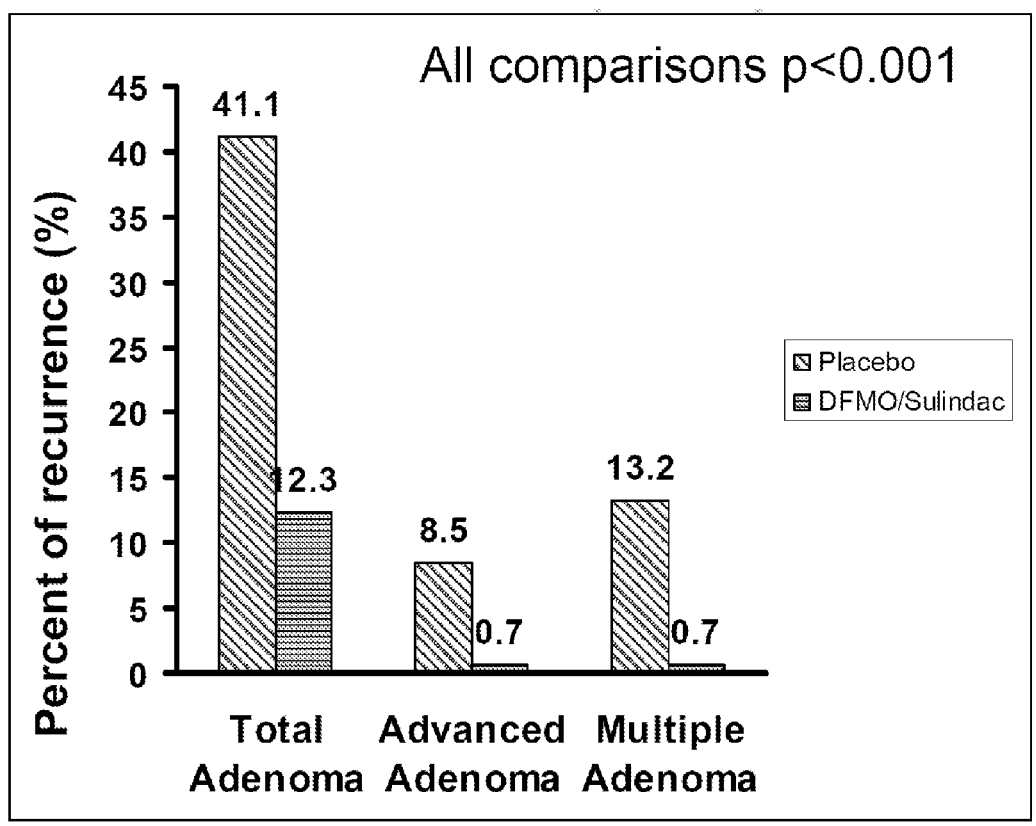
FIG. 6—Reduction in Adenomatous Polyps. This figure shows the percent recurrence of adenomatous polyps of patients were treated with DFMO and Sulindac compared with placebo. There was a 70% reduction in total adenoma, a 92% reduction in advanced adenoma, and 95% reduction in multiple adenoma.
Figure 7:
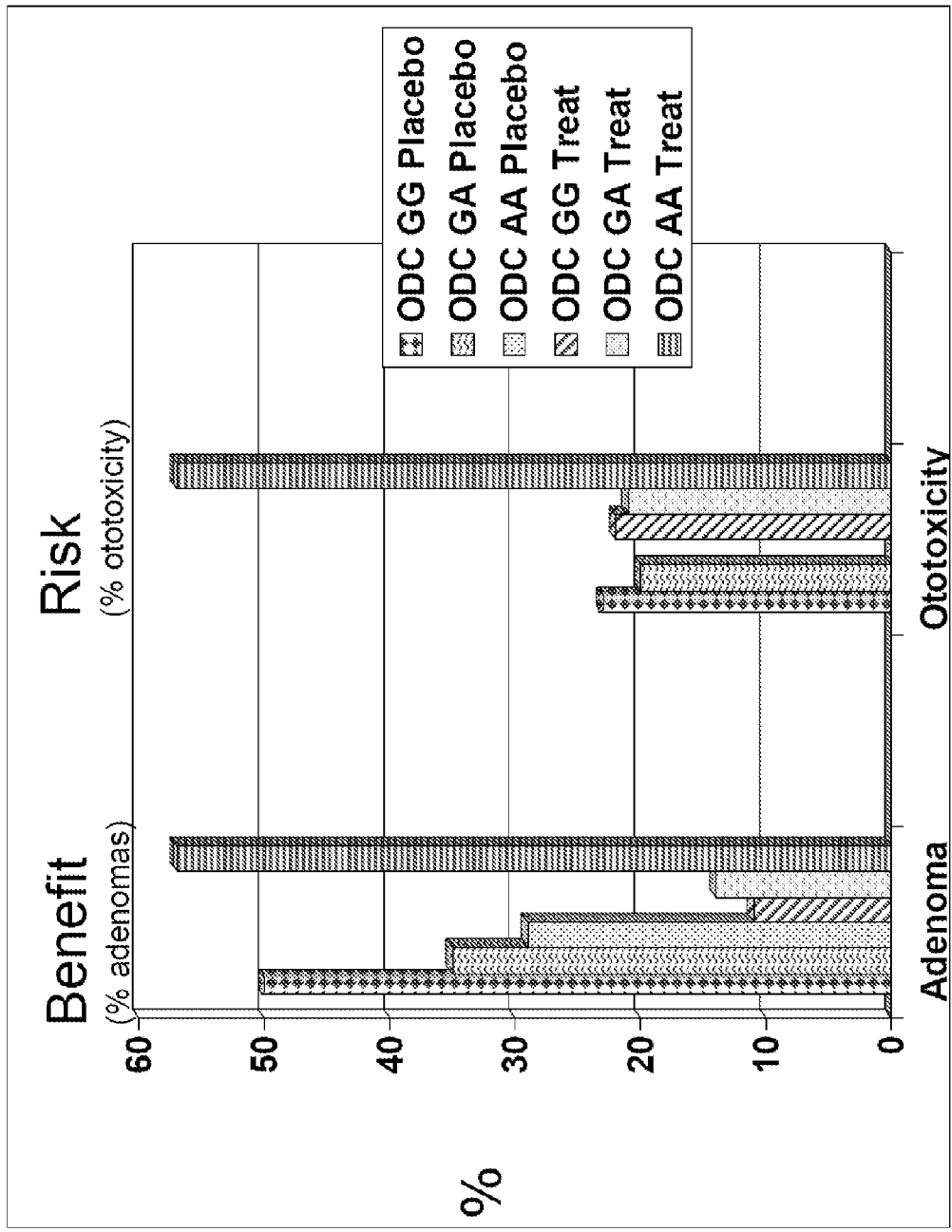
FIG. 7—Pharmacogenomic Benefit/Risk Analysis Based on +316 ODC1 Genotype. This figure compares reduction in % recurrence of adenomas at the end of 3 years versus placebo, with % ototoxicity for treatment and placebo groups as a function of the patient's+316 ODC1 genotype. Ototoxicity was determined using audiometric testing.
Figure 8:
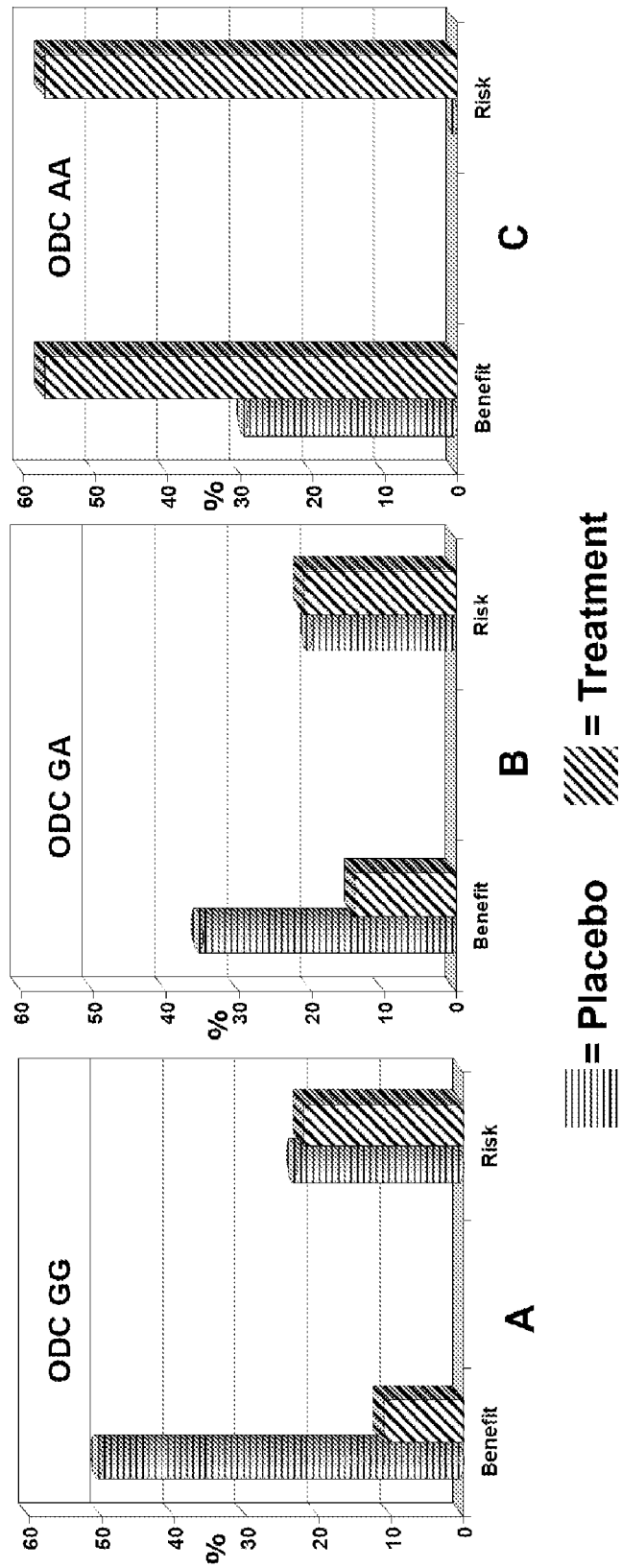
FIG. 8A-C—Pharmacogenomic Benefit/Risk Analysis Based on +316 ODC1 Genotype. This figure compares benefit, reduction in % recurrence of adenomas at the end of 3 years, with risk, % ototoxicity, for treatment and placebo groups as a function of the patient's+316 ODC1 genotype. Ototoxicity was determined using audiometric testing.

ODC allele-specific promoter activity was assessed. The hypothesis that +316 ODC SNP influenced ODC expression in a manner dependant on the expression of E-box activators and repressors was tested as follows. Transient co-transfection of colon cancer-derived HT29 cells was accomplished with ODC allele-specific promoter constructs in combination with vectors expressing either the transcriptional activator c-MYC or the repressor MAD1 (FIGS. 4A & B). The standard error bars shown reflect the variability in triplicate measurements within a single representative experiment, which has been replicated. The allele-specific promoter-reporters used in these experiments included all three E-boxes shown in FIG. 2A. As shown in FIG. 4A, c-MYC expression had the greatest stimulatory effect on promoters containing three consensus E-boxes and the ODC-A allele (wt E-box1 +316 A, P=0.0014). Deletion of the upstream E-box reduced promoter activity, but c-MYC expression continued to stimulate this activity (mut E-box1 +316 A, P=0.0013). Substitution of a G for the A at the +316 SNP position reduced the ability of c-MYC to stimulate promoter activity even with an intact 5' flanking consensus E-box. Mutation of the 5' flanking consensus E-box in combination with the ODC-G allele further reduced promoter activity.

When MAD1, rather than c-MYC, was co-transfected with the ODC allele-specific promoter reporters (FIG. 4B), the repressor was only able to reduce the activity of the ODC promoter which contained all three E-boxes and the wild-type +316 A-allele (P=0.027). Deletion of the upstream E-box (mut E-box1 +316A) significantly reduced the effect of MAD1 on ODC promoter activity. Substitution of G for A at the +316 position rendered promoters containing either two or three E-boxes unresponsive to MAD1 suppression.

IV. Difluoromethylornithine (DFMO)

DFMO, also know as eflornithine, has the following chemical designation; 2-(difluoromethyl)-dl-ornithine. It is an enzyme-activated irreversible inhibitor of ornithine decarboxylase (ODC), the rate limiting enzyme of the polyamine biosynthetic pathway. As a result of this inhibition of polyamine synthesis, the compound is effective in preventing cancer formation in many organ systems, inhibiting cancer growth, and reducing tumor size. It also has synergistic action with other antineoplastic agents.

DFMO has been shown to decrease APC-dependent intestinal tumorigenesis in mice (Erdman et al., 1999). Oral DFMO administered daily to humans inhibits ODC enzyme activity and polyamine contents in a number of epithelial tissues (Love et al., 1993; Gerner et al., 1994; Meyskens et al., 1994; Meyskens et al., 1998; Simoneau et al., 2001; Simoneau et al., 2008). Recently, the inventors reported that DFMO in combination with the non-steroidal anti-inflammatory drug (NSAID) sulindac, has been reported to markedly lower the adenoma recurrence rate among individuals with colonic adenomas when compared to placebos in a randomized clinical trial (Meyskens et al., 2008).

DFMO was originally synthesized by Centre de Recherche Merrell, Strasbourg; Current FDA approvals include African sleeping sickness. High dose systemic IV dosage form—not marketed (Sanofi/WHO)

Hirsutis (androgen-induced excess hair growth) topical dosage form No oral formulations are currently approved.

DFMO and its use in the treatment of benign prostatic hypertrophy are described in two patents, U.S. Pat. Nos. 4,413,141, and 4,330,559. U.S. Pat. No. 4,413,141 describes DFMO as being a powerful inhibitor of ODC, both in vitro and in vivo. Administration of DFMO causes a decrease in putrescine and spermidine concentrations in cells in which these polyamines are normally actively produced. Additionally, DFMO has been shown to be capable of slowing neoplastic cell proliferation when tested in standard tumor models. U.S. Pat. No. 4,330,559 describes the use of DFMO and DFMO derivatives for the treatment of benign prostatic hypertrophy. Benign prostatic hypertrophy, like many disease states characterized by rapid cell proliferation, is accompanied by abnormal elevation of polyamine concentrations. The treatment described within this reference can be administered to a patient either orally, or parenterally.

DFMO can potentially be given continuously with significant anti-tumor effects. This drug is relatively non-toxic at low doses of 0.4 g/m$^2$/day to humans while producing inhibition of putrescine synthesis in tumors. Studies in a rat-tumor model demonstrate that DFMO infusion can produce a 90% decrease in tumor putrescine levels without suppressing peripheral platelet counts.

Side effects observed with DFMO include effects on hearing at high doses of 4 g/M$^2$/day that resolve when it is discontinued. These effects on hearing are not observed at lower doses of 0.4 g/M$^2$/day when administered for up to one year (Meyskens et al., 1994). In addition a few cases of dizziness/vertigo are seen that resolve when the drug is stopped. Thrombocytopenia has been reported predominantly in studies using high "therapeutic" doses of DFMO (>1.0 g/m$^2$/day) and primarily in cancer patients who had previously undergone chemotherapy or patients with compromised bone marrow. Although the toxicity associated with DFMO therapy are not, in general, as severe as other types of chemotherapy, in limited clinical trials it has been found to promote a dose-related thrombocytopenia. Moreover, studies in rats have shown that continuous infusion of DFMO for 12 days significantly reduces platelet counts compared with controls. Other investigations have made similar observations in which thrombocytopenia is the major toxicity of continuous i.v. DFMO therapy. These findings suggest that DFMO may significantly inhibit ODC activity of the bone marrow precursors of megakaryocytes. DFMO may inhibit proliferative repair processes, such as epithelial wound healing.

A phase III clinical trial assessed the recurrence of adenomatous polyps after treatment for 36 months with difluoromethylornithine (DFMO) plus sulindac or matched placebos. Temporary hearing loss is a known toxicity of treatment with DFMO, thus a comprehensive approach was developed to analyze serial air conduction audiograms. The generalized estimating equation method estimated the mean difference between treatment arms with regard to change in air conduction pure tone thresholds while accounting for within-subject correlation due to repeated measurements at frequencies.

Based on 290 subjects, there was an average difference of 0.50 dB between subjects treated with DFMO plus sulindac compared with those treated with placebo (95% confidence interval, −0.64 to 1.63 dB; P=0.39), adjusted for baseline values, age, and frequencies. In the normal speech range of 500 to 3,000 Hz, an estimated difference of 0.99 dB (−0.17 to 2.14 dB; P=0.09) was detected. Dose intensity did not add information to models. There were 14 of 151 (9.3%) in the DFMO plus sulindac group and 4 of 139 (2.9%) in the placebo group who experienced at least 15 dB hearing reduction from baseline in 2 or more consecutive frequencies across the entire range tested (P=0.02). Follow-up air conduction done at least 6 months after end of treatment showed an adjusted mean difference in hearing thresholds of 1.08 dB (−0.81 to 2.96 dB; P =0.26) between treatment arms. There was no significant difference in the proportion of subjects in the DFMO plus sulindac group who experienced clinically significant hearing loss compared with the placebo group. The estimated attributable risk of ototoxicity from exposure to the drug is 8.4% (95% confidence interval, −2.0% to 18.8%; P=0.12). There is a <2 dB difference in mean threshold for patients treated with DFMO plus sulindac compared with those treated with placebo. The results of this study are discussed in greater detail in McLaren et al., 2008, which is incorporated herein by reference in its entirety. Provided herein are methods of reducing and/or preventing ototoxicity in patients treated with agents such as DFMO and sulindac.

V. NSAIDs

NSAIDs are anti-inflammatory agents that are not steroids. In addition to anti-inflammatory actions, they have analgesic, antipyretic, and platelet-inhibitory actions. They are used primarily in the treatment of chronic arthritic conditions and certain soft tissue disorders associated with pain and inflammation. They act by blocking the synthesis of prostaglandins by inhibiting cyclooxygenase, which converts arachidonic acid to cyclic endoperoxides, precursors of prostaglandins Inhibition of prostaglandin synthesis accounts for their analgesic, antipyretic, and platelet-inhibitory actions; other mechanisms may contribute to their anti-inflammatory effects. Certain NSAIDs also may inhibit lipoxygenase enzymes or phospholipase C or may modulate T-cell function. (AMA Drug Evaluations Annual, 1814-5, 1994).

The nonsteroidal anti-inflammatory drugs (NSAIDs), including aspirin, ibuprofen, piroxicam (Reddy et al., 1990; Singh et al., 1994), indomethacin (Narisawa, 1981), and sulindac (Piazza et al., 1997; Rao et al., 1995), effectively inhibit colon carcinogenesis in the AOM-treated rat model. NSAIDs also inhibit the development of tumors harboring an activated Ki-ras (Singh and Reddy, 1995). NSAIDs appear to inhibit carcinogenesis via the induction of apoptosis in tumor cells (Bedi et al., 1995; Lupulescu, 1996; Piazza et al., 1995; Piazza et al., 1997b). A number of studies suggest that the chemopreventive properties of the NSAIDs, including the induction of apoptosis, is a function of their ability to inhibit prostaglandin synthesis (reviewed in DuBois et al., 1996; Lupulescu, 1996; Vane and Botting, 1997). Studies, however, indicate that NSAIDs may act through both prostaglandin-dependent and -independent mechanisms (Alberts et al., 1995; Piazza et al., 1997a; Thompson et al., 1995; Hanif, 1996). Sulindac sulfone, a metabolite of the NSAID sulindac, lacks COX-inhibitory activity yet induces apoptosis in tumor cells (Piazza et al., 1995; Piazza et al., 1997b) and inhibits tumor development in several rodent models of carcinogenesis (Thompson et al., 1995; Piazza et al., 1995, 1997a).

Several NSAIDs have been examined for their effects in human clinical trials. A phase IIa trial (one month) of ibuprofen was completed and even at the dose of 300 mg/day, a significant decrease in prostoglandin $E_2$ ($PGE_2$) levels in flat mucosa was seen. A dose of 300 mg of ibuprofen is very low (therapeutic doses range from 1200-3000 mg/day or more), and toxicity is unlikely to be seen, even over the long-term. However, in animal chemoprevention models, ibuprofen is less effective than other NSAIDs.

A. Sulindac and Its Major Metabolites, Sulindac Sulfone and Sulindac Sulfide

Sulindac is a non-steroidal, anti-inflammatory indene derivative with the following chemical designation; (Z)-5-fluoro-2-methyl-1-((4 (methylsulfin-yl)phenyl)methylene) 1H-indene-3-acetic acid (Physician's Desk Reference, 1999). The sulfinyl moiety is converted in vivo by reversible reduction to a sulfide metabolite and by irreversible oxidation to a sulfone metabolite (exisulind). See U.S. Pat. No. 6,258,845, which is incorporated herein by reference in its entirety. Sulindac, which also inhibits Ki-ras activation, is metabolized to two different molecules which differ in their ability to inhibit COX, yet both are able to exert chemopreventive effects via the induction of apoptosis. Sulindac sulfone lacks COX-inhibitory activity, and most likely facilitates the induction of apoptosis in a manner independent of prostaglandin synthesis. Available evidence indicates that the sulfide derivative is at least one of the biologically active compounds. Based on this, sulindac may be considered a prodrug.

Sulindac (Clinoril®) is available, for example, as 150 mg and 200 mg tablets. The most common dosage for adults is 150 to 200 mg twice a day, with a maximal daily dose of 400 mg. After oral administration, about 90% of the drug is absorbed. Peak plasma levels are achieved in about 2 hours in fasting patients and 3 to 4 hours when administered with food. The mean half-life of sulindac is 7.8 hours: the mean half-life of the sulfide metabolite is 16.4 hours. U.S. Pat. Nos. 3,647,858 and 3,654,349 cover preparations of sulindac, both are incorporate by reference herein in their entireties.

Sulindac is indicated for the acute and long-term relief of signs and symptoms of osteoarthritis, rheumatoid arthritis, ankylosing spondylitis, acute gout, and acute painful shoulder. The analgesic and antiinflammatory effects exerted by sulindac (400 mg per day) are comparable to those achieved by aspirin (4 g per day), ibuprofen (1200 mg per day), indometacin (125 mg per day), and phenylbutazone (400 to 600 mg per day). Side effects of sulindac include mild gastrointestinal effects in nearly 20% of patients, with abdominal pain and nausea being the most frequent complaints. CNS side effects are seen in up to 10% of patients, with drowsiness, headache, and nervousness being those most frequently reported. Skin rash and pruritus occur in 5% of patients. Chronic treatment with sulindac can lead to serious gastrointestinal toxicity such as bleeding, ulceration, and perforation.

The potential use of sulindac for chemoprevention of cancers, and in particular colorectal polyps, has been well studied. Two recent U.S. Pat. Nos. 5,814,625 and 5,843,929, detail potential chemopreventive uses of sulindac in humans. Both patents are incorporated herein in their entireties. Doses of sulindac claimed in U.S. Pat. No. 5,814,625 range from 10 mg to 1500 mg per day, with preferred doses of 50 mg to 500 mg per day. However, at the higher doses, the biggest problem with the use of sulindac as a single agent in chemoprevention is its well-known toxicities and moderately high risk of intolerance. The elderly appear to be especially vulnerable, as the incidence of side effects is higher in those over the age of 60. It is noted that this age group is most likely to develop colorectal cancer, and therefore, most likely to benefit from chemoprevention.

Sulindac and its sulfone metabolite exisulind have been tested and continue to be tested clinically for the prevention and treatment of several cancer types. Clinical Trials.gov, a U.S. National Institutes of Health database provides the following overview of as of May 10, 2010.

| Status | Clinical Trial | |
|---|---|---|
| Recruiting | A Randomized Study of Sulindac in Oral Premalignant Lesions | |
| | Conditions: | Leukoplakia, Oral; Benign Neoplasms |
| | Interventions: | Drug: sulindac; Drug: Placebo |
| | Sponsors: | Memorial Sloan-Kettering Cancer Center; |
| | | Head and Neck Surgery, AIMS, Cochin, India; |
| | | Weill Medical College of Cornell University; |
| | | Regional Cancer Centre (RCC), Trivandrum, India; |
| | | Mazumdar Shaw Cancer Center (MSCC) |
| | Phase: | Not listed |
| Recruiting | Sulindac in Preventing Melanoma in Healthy Participants Who Are at Increased Risk of Melanoma | |
| | Condition: | Precancerous Condition |
| | Interventions: | Drug: sulindac; Other: placebo |

| Status | Clinical Trial | |
|---|---|---|
| | Sponsors: | University of Arizona; National Cancer Institute (NCI) |
| | Phase: | Phase II |
| Active, not recruiting | Eflornithine and Sulindac in Preventing Colorectal Cancer in Patients With Colon Polyps | |
| | Conditions: | Colorectal Cancer; Precancerous/Nonmalignant Condition |
| | Intervention: | Drug: eflornithine plus sulindac |
| | Sponsors: | University of California, Irvine; Chao Family Comprehensive Cancer Center; National Cancer Institute (NCI) |
| | Phase: | Phase III |
| Completed | Sulindac in Preventing Breast Cancer in Women at High Risk for Breast Cancer | |
| | Condition: | Breast Cancer |
| | Interventions: | Drug: sulindac; Other: laboratory biomarker analysis |
| | Sponsors: | University of Arizona; National Cancer Institute (NCI) |
| | Phase: | Phase I |
| Completed | Sulindac Capsules Compared With Sulindac Tablets in Healthy Volunteers | |
| | Condition: | Unspecified Adult Solid Tumor, Protocol Specific |
| | Interventions: | Drug: sulindac; Other: pharmacological study |
| | Sponsors: | Mayo Clinic; National Cancer Institute (NCI) |
| | Phase: | |
| Active, not recruiting | Eflornithine Plus Sulindac in Preventing Colorectal Cancer in Patients With Benign Colorectal Polyps | |
| | Condition: | Colorectal Cancer |
| | Intervention: | Drug: eflornithine plus sulindac |
| | Sponsors: | University of California, Irvine; Chao Family Comprehensive Cancer Center; National Cancer Institute (NCI) |
| | Phase: | Phase II |
| Active, not recruiting | Bevacizumab/Tarceva and Tarceva/Sulindac in Squamous Cell Carcinoma of the Head and Neck | |
| | Condition: | Squamous Cell Carcinoma of the Head and Neck (SCCHN) |
| | Interventions: | Drug: Bevacizumab; Drug: erlotinib; Drug: Sulindac |
| | Sponsors: | Massachusetts General Hospital; Dana-Farber Cancer Institute; Emory University; University of North Carolina, Chapel Hill; Genentech; OSI Pharmaceuticals |
| | Phase: | Phase II |
| Active, not recruiting | Sulindac in Preventing Lung Cancer in Current or Former Smokers With Bronchial Dysplasia | |
| | Conditions: | Lung Cancer; Precancerous Condition; Tobacco Use Disorder |
| | Interventions: | Drug: sulindac; Other: placebo |
| | Sponsors: | Mayo Clinic; National Cancer Institute (NCI) |
| | Phase: | Phase II |
| Completed | Sulindac and Tamoxifen in Treating Patients With Desmoid Tumor | |
| | Condition: | Desmoid Tumor |
| | Interventions: | Drug: sulindac; Drug: tamoxifen citrate |
| | Sponsors: | Children's Oncology Group; National Cancer Institute (NCI) |
| | Phase: | Phase II |
| Recruiting | Sulindac and Epirubicin in Treating Patients With Metastatic Malignant Melanoma | |
| | Condition: | Melanoma (Skin) |
| | Interventions: | Drug: epirubicin hydrochloride; Drug: sulindac; Other: immunologic technique |
| | Sponsor: | All Ireland Cooperative Oncology Research Group |
| | Phase: | Phase II |
| Completed | Atorvastatin, Oligofructose-Enriched Inulin, or Sulindac in Preventing Cancer in Patients at Increased Risk of Developing Colorectal Neoplasia | |
| | Conditions: | Colorectal Cancer; Precancerous Condition |
| | Interventions: | Dietary Supplement: oligofructose-enriched inulin; Drug: atorvastatin calcium; Drug: sulindac; Other: placebo |
| | Sponsors: | Mayo Clinic; National Cancer Institute (NCI) |
| | Phase: | Phase II |
| Suspended | Sulindac and Plant Compounds in Preventing Colon Cancer | |
| | Condition: | Colorectal Cancer |
| | Interventions: | Dietary Supplement: curcumin; |

-continued

| Status | Clinical Trial | |
|---|---|---|
| | | Dietary Supplement: rutin; Drug: quercetin; Drug: sulindac |
| | Sponsor: | Rockefeller University |
| | Phase: | |
| Active, not recruiting | Comparison of Sulindac, Aspirin, and Ursodiol in Preventing Colorectal Cancer | |
| | Condition: | Colorectal Cancer |
| | Interventions: | Drug: acetylsalicylic acid; Drug: sulindac; Drug: ursodiol |
| | Sponsors: | M. D. Anderson Cancer Center; National Cancer Institute (NCI) |
| | Phase: | Phase II |
| Completed | Sulindac and Docetaxel in Treating Women With Metastatic or Recurrent Breast Cancer | |
| | Condition: | Breast Cancer |
| | Interventions: | Drug: docetaxel; Drug: sulindac |
| | Sponsors: | Fox Chase Cancer Center; National Cancer Institute (NCI) |
| | Phase: | Phase II |
| Recruiting | Influence of Sulindac and Probiotics on the Development of Pouch Adenomas in Patients With Familial Adenomatous Polyposis | |
| | Condition: | Adenomatous Polyposis Coli |
| | Interventions: | Drug: Sulindac (drug); Drug: VSL#3 (probiotic); Drug: Inulin (probiotic) |
| | Sponsors: | Radboud University; Dutch Cancer Society |
| | Phase: | Phase II |
| Terminated | The Effects of Curcuminoids on Aberrant Crypt Foci in the Human Colon | |
| | Condition: | Aberrant Crypt Foci |
| | Interventions: | Drug: sulindac; Drug: curcumin |
| | Sponsor: | University of Medicine and Dentistry New Jersey |
| | Phase: | |
| Recruiting | Use of Curcumin for Treatment of Intestinal Adenomas in Familial Adenomatous Polyposis (FAP) | |
| | Conditions: | Lower Tract Polyps in Patients With FAP; Upper Tract Polyps in Patients With FAP |
| | Interventions: | Drug: Calcumin (Curcumin); Other: Risk Factor Questionnaire; Other: Blood samples; Other: Biopsies (Sigmoidoscopy); Other: Biopsies (Upper endoscopy) |
| | Sponsor: | University of Puerto Rico |
| | Phase: | |
| Active, not recruiting | To Lengthen the Duration of the Off-Treatment of Intermittent Androgen Suppression | |
| | Condition: | Prostate Cancer |
| | Interventions: | Drug: Flutamide; Drug: Leuprolide Acetate; Drug: Exisulind |
| | Sponsors: | University of Washington; OSI Pharmaceuticals |
| | Phase: | Phase II |
| Completed | Safety, Efficacy and Pharmacokinetic Between Capecitabine and Exisulind in Metastatic Breast Cancer Patients | |
| | Conditions: | Breast Neoplasms; Metastases, Neoplasm |
| | Interventions: | Drug: Capecitabine; Drug: Exisulind |
| | Sponsors: | M. D. Anderson Cancer Center; Cell Pathways |
| | Phases: | Phase I/Phase II |
| Completed | Neoadjuvant Exisulind in Treating Patients Who Are Undergoing Radical Prostatectomy for Stage II or Stage III Prostate Cancer | |
| | Condition: | Prostate Cancer |
| | Interventions: | Drug: exisulind; Procedure: conventional surgery; Procedure: neoadjuvant therapy |
| | Sponsors: | Mayo Clinic; National Cancer Institute (NCI) |
| | Phase: | Phase II |
| Completed | Combination Chemotherapy in Treating Patients With Advanced Non-Small Cell Lung Cancer | |
| | Condition: | Lung Cancer |
| | Interventions: | Drug: carboplatin; Drug: exisulind; Drug: gemcitabine hydrochloride |
| | Sponsors: | Eastern Cooperative Oncology Group; National Cancer Institute (NCI) |
| | Phase: | Phase II |

| Status | Clinical Trial |
| --- | --- |
| Completed | Phase II Study of Taxotere in Combination With Exisulind in Non-Small Cell Lung Cancer (NSCLC) Patients<br>Condition: NSCLC<br>Intervention: Drug: Exisulind<br>Sponsor: OSI Pharmaceuticals<br>Phases: Phase I/Phase II |
| Completed | A Phase III Study of the Efficacy of Taxotere/Aptosyn Versus Taxotere/Placebo in Non-Small Cell Lung Cancer Patients<br>Condition: Non-Small Cell Lung Cancer<br>Intervention: Drug: Exisulind<br>Sponsor: OSI Pharmaceuticals<br>Phase: Phase III |
| Completed | Exisulind Versus Placebo After Surgical Removal of the Prostate<br>Condition: Prostatic Neoplasms<br>Intervention: Drug: Exisulind<br>Sponsors: Mayo Clinic; OSI Pharmaceuticals<br>Phase: Phase II |
| Completed | Docetaxel, Estramustine, and Exisulind in Treating Patients With Metastatic Prostate Cancer That Has Not Responded to Hormone Therapy<br>Condition: Prostate Cancer<br>Interventions: Drug: docetaxel;<br>Drug: estramustine phosphate sodium;<br>Drug: exisulind<br>Sponsors: Cancer and Leukemia Group B;<br>National Cancer Institute (NCI)<br>Phase: Phase II |
| Completed | Combination Chemotherapy and Exisulind in Treating Patients With Extensive-Stage Small Cell Lung Cancer<br>Condition: Lung Cancer<br>Interventions: Drug: carboplatin; Drug: etoposide;<br>Drug: exisulind<br>Sponsors: Cancer and Leukemia Group B;<br>National Cancer Institute (NCI)<br>Phase: Phase II |
| Active, not recruiting | Exisulind in Preventing Polyps in Patients With Familial Adenomatous Polyposis<br>Conditions: Colorectal Cancer;<br>Small Intestine Cancer<br>Intervention: Drug: exisulind<br>Sponsor: University of Utah<br>Phases: Phase II/Phase III |
| Completed | Exisulind Prior to Radical Prostatectomy<br>Condition: Prostatic Neoplasms<br>Intervention: Drug: Exisulind Therapy<br>Sponsors: Mayo Clinic;<br>National Cancer Institute (NCI)<br>Phase: Phase II |

B. Piroxicam

A non-steroidal anti-inflammatory agent that is well established in the treatment of rheumatoid arthritis and osteoarthritis with the following chemical designation; 4-hydroxy-2-methyl-$N^2$-pyridyl-2H-1,2-benzothiazine-3-carboxamide 1,1-dioxide. Its usefulness also has been demonstrated in the treatment of musculoskeletal disorders, dysmenorrhea, and postoperative pain. Its long half-life enables it to be administered once daily. The drug has been shown to be effective if administered rectally. Gastrointestinal complaints are the most frequently reported side effects.

Piroxicam has been shown to be effective chemoprevention agent in animal models (Pollard and Luckert, 1989; Reddy et al., 1987), although it demonstrated side effects in a recent IIb trial. A large meta-analysis of the side effects of the NSAIDs also indicates that piroxicam has more side effects than other NSAIDs (Lanza et al., 1995). Sulindac has been shown to produce regression of adenomas in Familial Adenomatous Polyposis (FAP) patients (Muscat et al., 1994), although at least one study in sporadic adenomas has shown no such effect (Ladenheim et al., 1995).

The combination of DFMO and piroxicam has been shown to have a synergistic chemopreventive effect in the AOM-treated rat model of colon carcinogenesis (Reddy et al., 1990), although DFMO exerted a greater suppressive effect than piroxicam on Ki-ras mutation and tumorigenesis when each agent was administered separately (Reddy et al., 1990). In one study, administration of DFMO or piroxicam to AOM-treated rats reduced the number of tumors harboring Ki-ras mutations from 90% to 36% and 25% respectively (Singh et al., 1994). Both agents also reduced the amount of biochemically active p21 ras in existing tumors.

C. Combinations of NSAIDs

Combinations of various NSAIDs are also used for various purposes. By using lower doses of two or more NSAIDs, it is possible to reduce the side effects or toxicities associated with higher doses of individual NSAIDs. For example, in some embodiments, sulindac may be used together with celecoxib. In some embodiments, the one or both of the NSAIDS are selective COX-2 inhibitors. Examples of NSAIDS that back be used either alone or in combination include, but are not limited to, the following: ibuprofen, naproxen, fenoprofen, ketoprofen, flurbiprofen, oxaprozin, indomethacin, sulindac, etodolac, diclofenac, piroxicam, meloxicam, tenoxicam, droxicam, lornoxicam, isoxicam, mefenamic acid, meclofenamic acid, flufenamic acid, tolfenamic acid, celecoxib rofecoxib valdecoxib parecoxib, lumiracoxib, or etoricoxib.

VI. Eflornithine/Sulindac Combination Therapy

Preclinical studies of chemoprevention drugs given in combination at low doses show remarkable efficacy in preventing adenomas with little additional toxicities, suggesting a strategy to improve risk to benefit ratios for preventing recurrent adenomas.

As noted above, the Min (multiple intestinal neoplasia) mouse, which shares a mutated APC/apc genotype with FAP, serves as a useful experimental animal model for human FAP patients (Lipkin, 1997). The Min mouse can develop greater than 100 gastrointestinal adenomas/adenocarcinomas throughout the gastrointestinal tract by 120 days of life leading to GI bleeding, obstruction and death. A combination therapy of DFMO and sulindac was shown to be effective in reducing adenomas in these mice (U.S. Pat. No. 6,258,845; Gerner and Meyskens, 2004). The results of treating Min mice with either DFMO alone, sulindac alone, or a combination of DFMO and sulindac on tumor formation in either the colon or small intestine are shown in FIGS. 9 & 10. FIG. 9 shows the average number of tumors by size in the colon of the three treatment groups compared to untreated controls. FIG. 10 shows the average number of tumors by size in the small intestine of the three treatment groups compared to untreated controls. FIG. 11 shows how the number of high grade adenomas various depending on therapy, single or combination.

VII. Efficacy of Polyamine-Inhibitory Therapy Based On Patient Profile

The efficacy of a polyamine-inhibitory combination of long-term daily oral D,L-α-difluoromethylornithine (DFMO, eflornithine) and sulindac among CRA patients was demonstrated (Meyskens et al., 2008), however, treatment was associated with modest, subclinical ototoxicity (McLaren et al., 2008), and a greater number of cardiovascular events among patients with high baseline cardiovascular risk (Zell et al., 2009). The inventors have now investigated determined that the ODC1 genotype differentially affects adenoma recurrence, tissue polyamine responses, or toxicity profiles after eflornithine and sulindac treatment compared to placebo.

Three hundred seventy-five patients with history of resected (>or =3 mm) adenomas were randomly assigned to receive oral difluoromethylornithine (DFMO) 500 mg and sulindac 150 mg once daily or matched placebos for 36 months, stratified by use of low-dose aspirin (81 mg) at baseline and clinical site. Follow-up colonoscopy was done 3 years after randomization or off-study. Colorectal adenoma recurrence was compared among the groups with log-binomial regression. Comparing the outcome in patients receiving placebos to those receiving active intervention, (a) the recurrence of one or more adenomas was 41.1% and 12.3% (risk ratio, 0.30; 95% confidence interval, 0.18-0.49; P<0.001); (b) 8.5% had one or more advanced adenomas, compared with 0.7% of patients (risk ratio, 0.085; 95% confidence interval, 0.011-0.65; P<0.001); and (c) 17 (13.2%) patients had multiple adenomas (>1) at the final colonoscopy, compared with 1 (0.7%; risk ratio, 0.055; 0.0074-0.41; P<0.001). Serious adverse events (grade >or=3) occurred in 8.2% of patients in the placebo group, compared with 11% in the active intervention group (P=0.35). There was no significant difference in the proportion of patients reporting hearing changes from baseline. Recurrent adenomatous polyps can be markedly reduced by a combination of low oral doses of DFMO and sulindac and with few side effects. The details of this study are discussed in greater detail below and in Meyskens et al., 2008, which is incorporated herein by reference in its entirety.

The study was halted by the Data Safety Monitoring Board (DSMB) after 267 patients completed end-of-study colonoscopies (due to the study meeting its efficacy endpoints). The DSMB monitored all safety and efficacy endpoints. As discussed in greater detail in the Examples, section this study involves analysis of patient data from the multi-center phase III colon adenoma prevention trial. See also (Meyskens et al., 2008), which is incorporated herein by reference in its entirety.

A. ODC1 Genotype Distribution

A total of 440 colorectal cancer (CRC) cases identified from the UC Irvine CRC gene-environment study were used in the case-only analysis. Median follow-up duration was 11 years. There were 270 (61%) colon cancer cases, 162 (37%) rectal cancer cases, and 8 (2%) CRC cases of unspecified location. Clinicopathologic data for colon and rectal cancer cases are shown in Table 1. ODC +316 genotype distribution among all CRC cases was 53% GG, 41% GA, and 7% AA. ODC +316 genotype distribution was similar among CRC cases with and without a family history. There were no significant differences in ODC genotype distribution by age (P=0.38), gender (P=0.56), family history (P=0.94), site within the colorectum (P=0.55), histology (P=0.46) or tumor grade (P=0.73). ODC genotype distribution did not significantly differ by stage at diagnosis: stage I (49% GG, 42% GA, 8% AA), stage II (56% GG, 38% GA, 6% AA), stage III (51% GG, 43% GA, 6% AA), stage IV (59% GG, 37% GA, 4% AA) (P=0.87). ODC genotype distribution by ethnicity revealed significant differences: Caucasian (382 cases: 53% GG, 41% GA, 6% AA, minor-A allele frequency=26%), African-American (7 cases: 71% GG, 29% GA, 0% AA, minor-A allele frequency=15%), Hispanics (21 cases: 57% GG, 43% GA, 0% AA, minor-A allele frequency=21%), and Asians (27 cases: 33% GG, 41% GA, 26% AA, minor-A allele frequency=46%) (P=0.009). However, within each race ODC genotype distribution was in Hardy-Weinberg equilibrium (Caucasians P=0.36, African-Americans P=0.66, Hispanics P=0.21, Asians P=0.35).

B. Adenoma Recurrence

ODC1 genotype distribution was: 126 GG (55%), 87 GA (38%), and 15 AA (7%). Baseline clinical characteristics revealed differences, as shown in Table 1. In regression models with predictors age, gender, race, aspirin use, treatment, ODC1 genotype, and treatment, treatment was the only factor associated with differences in adenoma recurrence, tissue polyamine response, and ototoxicity. A statistically significant interaction was detected for ODC 1 genotype and treatment in the full model for adenoma recurrence (P=0.021), such that the pattern of adenoma recurrence among placebo patients was: GG-50%, GA-35%, AA-29% versus eflornithine/sulindac patients: GG-11%, GA-14%, AA-57%.

A statistically significant interaction was detected between ODC1 genotype and treatment in this model (P=0.038). ODC1 genotype was not significantly associated with a tissue putrescine response or spermidine:spermine ratio response in the full regression models (data not shown). The relative risk (RR) for adenoma recurrence related to treatment after adjustment in the full regression model was 0.39 (95% CI 0.24-0.66). There were no significant associations between treatment and ODC1 genotype group with regard to cardiovascular or gastrointestinal adverse events (Tables 3 & 4).

Here it was observed that the adenoma-inhibitory effect of eflornithine and sulindac was greater among those with the major G homozygous ODC1 genotype, in contrast to prior reports showing decreased risk of recurrent adenoma among CRA patients receiving aspirin carrying at least one A-allele (Martinez et al., 2003; Barry et al., 2006; Hubner et al., 2008) ODC1 genotype distribution was similar to that reported in prior aspirin-based trials (Martinez et al., 2003; Barry et al., 2006; Hubner et al., 2008), and the A-allele was associated with a non-significant lower recurrent adenoma risk in the placebo group consistent with previous reports (Martinez et al., 2003; Hubner et al., 2008). These results demonstrate that ODC1 A-allele carriers differ in response to prolonged exposure with eflornithine and sulindac compared to GG genotype patients, with A-allele carriers experiencing less benefit in terms of adenoma recurrence, and potential for elevated risk of developing ototoxicity, especially among the AA homozygotes.

C. Survival Analysis

Of the 440 CRC cases, 138 (31%) were deceased at the time of analysis. Sixty-four (46%) deaths occurred in cases carrying the GG genotype, compared to 74 (54%) deaths in cases with the AA/AG genotypes. Cause of death was available for 102 of the 138 deceased CRC cases. Eighty-five (83%) CRC cases died as a result of CRC. A statistically significant improvement in CRC-specific survival was observed among all CRC cases homozygous for the ODC G-allele (10-year survival=84%) compared to cases with at least one A-allele (ODC GA/AA) (10-year survival=76%; P=0.031). CRC-specific survival analysis by stage revealed that significantly different survival differences were not observed for AJCC stage I (P=0.055), II (P=0.61), or IV (P=0.65) CRC. However, among cases with stage III CRC the ODC GG genotype was associated with improved 10-year CRC-specific survival: 75% compared to 60% for ODC GA/AA genotype cases; P=0.024 (FIG. 1). Among colon cancer cases, a statistically significant CRC-specific survival benefit was observed for those with ODC GG genotype compared to ODC GA/AA cases (10-year survival rate=87% vs. 79%; P=0.029); this was not observed for rectal cancer cases (10-year survival=78% for ODC GG cases vs. 72% for ODC GA/AA cases; P=0.42).

Among all CRC cases, the CRC-specific survival estimates based on ODC genotype after adjustment for age (years), gender, ethnicity, family history of CRC, TNM stage at diagnosis, tumor site within the colon, histologic subtype, treatment with surgery, radiation therapy, and chemotherapy were a follows: ODC GG hazards ratio (HR)=1.00 (referent), ODC GA HR=1.73, and ODC AA genotype HR=1.73 (P-trend=0.0283). Among colon cases only, CRC-specific survival analysis revealed that the ODC +316 SNP was an independent predictor of CRC-specific survival, after adjustment for the above clinical variables. Compared to ODC GG colon cancer cases, the CRC-specific risk of death (HR) was 2.31 (1.15-4.64) for ODC GA genotype and 3.73 (0.93-14.99) for ODC AA genotype (P-trend=0.006) (Table 2). Overall survival analysis of these colon cancer cases was consistent with the CRC-specific survival analysis (Table 2). Among rectal cancer cases, CRC-specific survival analysis revealed that the ODC +316 SNP was not an independent predictor of CRC-specific survival after adjustment for the aforementioned clinical variables. Compared to ODC GG rectal cancer cases (HR=1.00, reference), the CRC-specific risk of death (HR) was 1.72 (0.83-3.57) for ODC GA heterozygotes and 1.93 (0.56-6.67) for ODC AA homozygotes (P-trend=0.12).

As noted above, the ODC +316 genotype distribution differed across ethnicity. The observed mortality risk, other than by chance, likely reflects differences based on ODC genotype, however the risk may be restricted to a particular ethnic group. Thus multivariate analyses were conducted among Caucasian colon cancer cases, to assess genotype-specific mortality risk within this single ethnic group. Among the 234 Caucasian colon cancer cases, there were 37 CRC-related deaths. Multivariate CRC-specific survival analysis revealed that the ODC +316 SNP was an independent predictor of CRC-specific survival among Caucasian colon cancer cases after adjustment for the aforementioned relevant clinical variables. Compared to cases with ODC GG genotype (HR=1.00, reference), the CRC-specific risk of death (HR) was 2.67 (1.22-5.82) for ODC GA genotype and 6.28 (1.46-26.95) for ODC AA genotype (P-trend=0.0018).

Genotype-specific survival differences among CRC cases were limited to colon cancer cases: compared to ODC GG genotype cases (HR=1.00, reference) the adjusted CRC-SS hazards ratio (HR) was 2.31 (1.15-4.64) for ODC GA cases and 3.73 (0.93-14.99) for ODC AA cases (P-trend=0.006). In colon cancer cells, the ODC +316 SNP, flanked by two E-boxes, predicts ODC promoter activity. The E-box activator c-MYC and repressors MAD1 and MAD4 preferentially bind to minor A-, compared to major G-, alleles in cultured cells.

Based on this population-based analysis of colorectal cancer cases with eleven years follow-up duration, it was observed that the +316 ODC SNP was associated with colorectal cancer specific survival among colon cancer cases. A statistically significant increased risk of CRC-specific mortality was observed with each additional ODC A-allele among colon cancer cases, i.e., from ODC GG to GA to AA (P-trend=0.006), after adjustment for age, gender, ethnicity, tumor stage, family history of CRC, tumor site, histology, treatment with surgery, radiation therapy, and chemotherapy.

D. Allele Specific Regulation of Transcription Factors

The experimental data presented here provide insights into potential biologic mechanisms underlying our clinical observations. In colon cancer epithelial cells, we have shown that the ODC +316 SNP is functionally significant, as evidenced by increased binding of E-box transcription factors to promoter elements containing A-, compared to G-, alleles. Both the activator c-MYC and the repressor MAD1 show greater effects on promoter activity in reporter elements containing A- versus G- alleles. These results suggest allele-specific regulation of ODC by E-box transcription factors. ODC protein enzyme activity is not apparently affected by the ODC +316 SNP genotype, which we believe influences ODC transcription.

In colon cells, it has been shown that conditional expression of wild type APC, a gene expressed in normal colonic mucosa, suppresses c-MYC, and increases MAD1, expression (Fultz and Gerner, 2002). Further, it has have reported that wild type APC can regulate ODC promoter activity in a manner dependent on the +316 SNP (Martinez et al., 2003). Wild type APC is expressed in the apparently normal colonic mucosa of individuals not afflicted with FAP, while the majority of sporadic colon adenomas show evidence of mutated or deleted APC (Iwamoto et al., 2000). MYC is expressed at low levels in normal intestinal mucosa but is increased in intestinal adenomas of $APC^{Min/+}$ mice. Conditional knockout of intestinal epithelial MYC expression suppresses intestinal tumorigenesis in $APC^{Min/+}$ mice (Ignatenko et al., 2006). As described above, previous work by our group (Martinez et al., 2003) and others (Hubner et al., 2008) demonstrated a protective role for the ODC A-allele, especially in aspirin users, against recurrence of colon polyps in clinical prevention trials. However, in the population-based study presented here, the ODC A-allele was associated with poor survival. This apparent contradiction may be explained by the results shown here, which indicate that both E-box activators and repressors bind the ODC A-allele selectively. The inventors speculate that the transition from normal epithelium, expressing E-box repressors, to neoplastic epithelium may be retarded in individuals with ODC A-alleles. This effect may result from suppression of polyamine synthesis. However, if the transformed epithelium begins to express E-box activators (such as c-MYC), then cancer progression may be more likely to occur in individuals with the ODC A genotype. Our results for risk of colon cancer-specific mortality are consistent with those of others showing that risk of prostate cancer may be associated with the ODC A-allele among specific individuals as the result of gene environment interactions (O'Brien et al., 2004; Visvanathan et al., 2004). Such colon cancer progression could be due to enhanced polyamine synthesis, as has been demonstrated already for prostate cancer (Simoneau et al., 2008).

This finding that a factor, such as the ODC SNP, may have both promoting and inhibiting effects on carcinogenesis is not unique. For example, transforming growth factor-beta (TGF-β) has diverse roles in carcinogenesis and cancer progression (Derynck et al., 2001; Pardali and Moustakas, 2007; Roberts and Wakefield, 2003). TGF-β in untransformed cells inhibits cell proliferation and induces apoptosis. Yet, it is overexpressed in all human tumors and is associated with late cancer progression, specifically tumor invasion and metastasis. A single study reporting ODC activity in human colorectal tumors demonstrated that high levels of ODC expression was significantly associated with improved survival (Matsubara et al., 1995). This suggests that, although ODC overexpression promotes the formation of human colorectal adenomas, it is possible that in established lesions, ODC overexpression causes enhanced proliferation and is associated with improved response to anti-proliferative treatments. However, that study did not include stratification by ODC genotype, so it is not known if these effects are independent of ODC genotype.

The observed associations of the ODC +316 SNP with CRC-specific mortality were limited to colon cancer cases. Among colon cancer cases, particularly strong effects were observed for Caucasians. Similar to other reports, the ODC +316 SNP allele frequency differs considerably by ethnicity (O'Brien et al., 2004). When the inventors limited the survival analysis to Caucasians only (i.e., the only ethnic group with adequate power for such analyses), the associations of the ODC +316 SNP were significant, and of greater magnitude than the estimates observed for the entire cohort.

The epidemiologic study shares limitations of other population-based analyses, including lack of data on comorbid conditions, performance status, and particular chemotherapeutic regimens utilized. Additionally, the tissue biopsy samples obtained from participants of the UC Irvine Gene-Environment Study of Familial Colorectal Cancer are paraffin-embedded specimens and therefore cannot be used for accurate assessment of tissue polyamine quantification by high performance liquid chromatography (HPLC). There is also the potential for selection bias, favoring a relatively healthy group of CRC survivors, since there was a median 16 month delay from the time of CRC diagnosis until study enrollment. Other factors affecting polyamine metabolism that were not accounted for in the present study may explain our observations. For example, aspirin activates polyamine acetylation and export and works with the ODC A-allele to reduce cell and tissue polyamine contents (Gerner et al., 2004; Martinez et al., 2003; Babbar et al., 2006).

In summary, the inventors have observed clinical consequences of the ODC +316 SNP on CRC-specific mortality among colon cancer cases. Additionally, the inventors have further established the functional significance of the ODC +316 SNP in the c-MYC- and MAW-dependent transcription of this gene in human colon cancer cells. Together, these experimental and epidemiologic findings suggest roles for the ODC +316 SNP in progression of colon cancer that are distinct from its previously reported role in progression to colon adenomas. These findings may be used to assess risk of colon cancer progression and may be used to direct patient-specific pharmacogenetic management, surveillance monitoring, and inform novel targeted approaches to secondary and tertiary colon cancer prevention.

E. Summary

A statistically significant interaction was detected for ODC1 genotype and treatment in the full model for adenoma recurrence (P=0.021), such that the pattern of adenoma recurrence among placebo patients was: GG-50%, GA-35%, AA-29% versus eflornithine/sulindac patients: GG-11%, GA-14%, AA-57%. Here it was observed that the adenoma-inhibitory effect of eflornithine and sulindac was greater among those with the major G homozygous ODC1 genotype, in contrast to prior reports showing decreased risk of recurrent adenoma among CRA patients receiving aspirin carrying at least one A-allele (Martinez et al., 2003; Barry et al., 2006; Hubner et al., 2008) These results demonstrate that ODC1 A-allele carriers differ in response to prolonged exposure with eflornithine and sulindac compared to GG genotype patients, with A-allele carriers experiencing less benefit in terms of adenoma recurrence, and potential for elevated risk of developing ototoxicity, especially among the AA homozygotes.

VIII. Polymorphism Analysis

The genotype at the +316 position of the ODC1 promoter gene of patient can determined using the methods provided below, including the specific methods described in the Examples section. These methods can be further modified and optimized using the principles and techniques of molecular biology as applied by a person skilled in the art. Such principles and techniques are taught, for example, in Small et al., (2002), which is incorporated herein by reference. General methods employed for the identification of single nucleotide polymorphisms (SNPs) are provided below. The reference of Kwok and Chen (2003) and Kwok (2001) provide overviews of some of these methods; both of these references are specifically incorporated by reference.

SNPs relating to ODC1 can be characterized by the use of any of these methods or suitable modification thereof. Such methods include the direct or indirect sequencing of the site, the use of restriction enzymes where the respective alleles of the site create or destroy a restriction site, the use of allele-specific hybridization probes, the use of antibodies that are specific for the proteins encoded by the different alleles of the polymorphism, or any other biochemical interpretation.

A. DNA Sequencing

A commonly used method of characterizing a polymorphism is direct DNA sequencing of the genetic locus that flanks and includes the polymorphism. Such analysis can be accomplished using either the "dideoxy-mediated chain termination method," also known as the "Sanger Method" (Sanger et al., 1975) or the "chemical degradation method," also known as the "Maxam-Gilbert method" (Maxam et al., 1977). Sequencing in combination with genomic sequence-specific amplification technologies, such as the polymerase chain reaction may be utilized to facilitate the recovery of the desired genes (Mullis et al., 1986; European Patent Application 50,424; European Patent Application. 84,796, European Patent Application 258,017, European Patent Application. 237,362; European Patent Application. 201,184; U.S. Pat. Nos. 4,683,202; 4,582,788; and 4,683,194), all of the above incorporated herein by reference.

B. Exonuclease Resistance

Other methods that can be employed to determine the identity of a nucleotide present at a polymorphic site utilize a specialized exonuclease-resistant nucleotide derivative (U.S. Patent. 4,656,127). A primer complementary to an allelic sequence immediately 3'-to the polymorphic site is hybridized to the DNA under investigation. If the polymorphic site on the DNA contains a nucleotide that is complementary to the particular exonucleotide-resistant nucleotide derivative present, then that derivative will be incorporated by a polymerase onto the end of the hybridized primer. Such incorporation makes the primer resistant to exonuclease cleavage and thereby permits its detection. As the identity of the exonucleotide-resistant derivative is known one can determine the specific nucleotide present in the polymorphic site of the DNA.

C. Microsequencing Methods

Several other primer-guided nucleotide incorporation procedures for assaying polymorphic sites in DNA have been described (Komher et al., 1989; Sokolov, 1990; Syvanen 1990; Kuppuswamy et al., 1991; Prezant et al., 1992; Ugozzoll et al., 1992; Nyren et al., 1993). These methods rely on the incorporation of labeled deoxynucleotides to discriminate between bases at a polymorphic site. As the signal is proportional to the number of deoxynucleotides incorporated, polymorphisms that occur in runs of the same nucleotide result in a signal that is proportional to the length of the run (Syvanen et al., 1990).

D. Extension in Solution

French Patent 2,650,840 and PCT Application WO91/02087 discuss a solution-based method for determining the identity of the nucleotide of a polymorphic site. According to these methods, a primer complementary to allelic sequences immediately 3'-to a polymorphic site is used. The identity of the nucleotide of that site is determined using labeled dideoxynucleotide derivatives which are incorporated at the end of the primer if complementary to the nucleotide of the polymorphic site.

E. Genetic Bit Analysis or Solid-Phase Extension

PCT Application WO92/15712 describes a method that uses mixtures of labeled terminators and a primer that is complementary to the sequence 3' to a polymorphic site. The labeled terminator that is incorporated is complementary to the nucleotide present in the polymorphic site of the target molecule being evaluated and is thus identified. Here the primer or the target molecule is immobilized to a solid phase.

F. Oligonucleotide Ligation Assay (OLA)

This is another solid phase method that uses different methodology (Landegren et al., 1988). Two oligonucleotides, capable of hybridizing to abutting sequences of a single strand of a target DNA are used. One of these oligonucleotides is biotinylated while the other is detectably labeled. If the precise complementary sequence is found in a target molecule, the oligonucleotides will hybridize such that their termini abut, and create a ligation substrate. Ligation permits the recovery of the labeled oligonucleotide by using avidin. Other nucleic acid detection assays, based on this method, combined with PCR have also been described (Nickerson et al., 1990). Here PCR is used to achieve the exponential amplification of target DNA, which is then detected using the OLA.

G. Ligase/Polymerase-Mediated Genetic Bit Analysis

U.S. Pat. No. 5,952,174 describes a method that also involves two primers capable of hybridizing to abutting sequences of a target molecule. The hybridized product is formed on a solid support to which the target is immobilized. Here the hybridization occurs such that the primers are separated from one another by a space of a single nucleotide. Incubating this hybridized product in the presence of a polymerase, a ligase, and a nucleoside triphosphate mixture containing at least one deoxynucleoside triphosphate allows the ligation of any pair of abutting hybridized oligonucleotides. Addition of a ligase results in two events required to generate a signal, extension and ligation. This provides a higher specificity and lower "noise" than methods using either extension or ligation alone and unlike the polymerase-based assays, this method enhances the specificity of the polymerase step by combining it with a second hybridization and a ligation step for a signal to be attached to the solid phase.

H. Invasive Cleavage Reactions

Invasive cleavage reactions can be used to evaluate cellular DNA for a particular polymorphism. A technology called INVADER® employs such reactions (e.g., de Arruda et al., 2002; Stevens et al., 2003, which are incorporated by reference). Generally, there are three nucleic acid molecules: 1) an oligonucleotide upstream of the target site ("upstream oligo"), 2) a probe oligonucleotide covering the target site ("probe"), and 3) a single-stranded DNA with the target site ("target"). The upstream oligo and probe do not overlap but they contain contiguous sequences. The probe contains a donor fluorophore, such as fluoroscein, and an acceptor dye, such as Dabcyl. The nucleotide at the 3' terminal end of the upstream oligo overlaps ("invades") the first base pair of a probe-target duplex. Then the probe is cleaved by a structure-specific 5' nuclease causing separation of the fluorophore/quencher pair, which increases the amount of fluorescence that can be detected. See Lu et al., 2004.

In some cases, the assay is conducted on a solid-surface or in an array format.

I. Other Methods To Detect SNPs

Several other specific methods for polymorphism detection and identification are presented below and may be used as such or with suitable modifications in conjunction with identifying polymorphisms of the ODC1 gene in the present invention. Several other methods are also described on the SNP web site of the NCBI on the World Wide Web at ncbi.nlm.nih.gov/SNP, incorporated herein by reference.

In a particular embodiment, extended haplotypes may be determined at any given locus in a population, which allows one to identify exactly which SNPs will be redundant and which will be essential in association studies. The latter is referred to as 'haplotype tag SNPs (htSNPs)', markers that capture the haplotypes of a gene or a region of linkage disequilibrium. See Johnson et al. (2001) and Ke and Cardon (2003), each of which is incorporated herein by reference, for exemplary methods.

The VDA-assay utilizes PCR amplification of genomic segments by long PCR methods using TaKaRa LA Taq reagents and other standard reaction conditions. The long amplification can amplify DNA sizes of about 2,000-12,000 bp. Hybridization of products to variant detector array (VDA) can be performed by a Affymetrix High Throughput Screening Center and analyzed with computerized software.

A method called Chip Assay uses PCR amplification of genomic segments by standard or long PCR protocols. Hybridization products are analyzed by VDA, Halushka et al. (1999), incorporated herein by reference. SNPs are generally classified as "Certain" or "Likely" based on computer analysis of hybridization patterns. By comparison to alternative detection methods such as nucleotide sequencing, "Certain" SNPs have been confirmed 100% of the time; and "Likely" SNPs have been confirmed 73% of the time by this method.

Other methods simply involve PCR amplification following digestion with the relevant restriction enzyme. Yet others involve sequencing of purified PCR products from known genomic regions.

In yet another method, individual exons or overlapping fragments of large exons are PCR-amplified. Primers are designed from published or database sequences and PCR-amplification of genomic DNA is performed using the following conditions: 200 ng DNA template, 0.5 µM each primer, 80 µM each of dCTP, dATP, dTTP and dGTP, 5% formamide, 1.5 mM MgCl$_2$, 0.5 U of Taq polymerase and 0.1 volume of the Taq buffer. Thermal cycling is performed and resulting PCR-products are analyzed by PCR-single strand conformation polymorphism (PCR-SSCP) analysis, under a variety of conditions, e.g, 5 or 10% polyacrylamide gel with 15% urea, with or without 5% glycerol. Electrophoresis is performed overnight. PCR-products that show mobility shifts are reamplified and sequenced to identify nucleotide variation.

In a method called CGAP-GAI (DEMIGLACE), sequence and alignment data (from a PHRAP.ace file), quality scores for the sequence base calls (from PHRED quality files), distance information (from PHYLIP dnadist and neighbour programs) and base-calling data (from PHRED '-d' switch) are loaded into memory. Sequences are aligned and examined for each vertical chunk ('slice') of the resulting assembly for disagreement. Any such slice is considered a candidate SNP (DEMIGLACE). A number of filters are used by DEMIGLACE to eliminate slices that are not likely to represent true polymorphisms. These include filters that: (i) exclude sequences in any given slice from SNP consideration where neighboring sequence quality scores drop 40% or more; (ii) exclude calls in which peak amplitude is below the fifteenth percentile of all base calls for that nucleotide type; (iii) disqualify regions of a sequence having a high number of disagreements with the consensus from participating in SNP calculations; (iv) removed from consideration any base call with an alternative call in which the peak takes up 25% or more of the area of the called peak; (v) exclude variations that occur in only one read direction. PHRED quality scores were converted into probability-of-error values for each nucleotide in the slice. Standard Baysian methods are used to calculate the posterior probability that there is evidence of nucleotide heterogeneity at a given location.

In a method called CU-RDF (RESEQ), PCR amplification is performed from DNA isolated from blood using specific primers for each SNP, and after typical cleanup protocols to remove unused primers and free nucleotides, direct sequencing using the same or nested primers.

In a method called DEBNICK (METHOD-B), a comparative analysis of clustered EST sequences is performed and confirmed by fluorescent-based DNA sequencing. In a related method, called DEBNICK (METHOD-C), comparative analysis of clustered EST sequences with phred quality >20 at the site of the mismatch, average phred quality >=20 over 5 bases 5'-FLANK and 3' to the SNP, no mismatches in 5 bases 5' and 3' to the SNP, at least two occurrences of each allele is performed and confirmed by examining traces.

In a method identified by ERO (RESEQ), new primers sets are designed for electronically published STSs and used to amplify DNA from 10 different mouse strains. The amplification product from each strain is then gel purified and sequenced using a standard dideoxy, cycle sequencing technique with $^{33}$P-labeled terminators. All the ddATP terminated reactions are then loaded in adjacent lanes of a sequencing gel followed by all of the ddGTP reactions and so on. SNPs are identified by visually scanning the radiographs.

In another method identified as ERO (RESEQ-HT), new primers sets are designed for electronically published murine DNA sequences and used to amplify DNA from 10 different mouse strains. The amplification product from each strain is prepared for sequencing by treating with Exonuclease I and Shrimp Alkaline Phosphatase. Sequencing is performed using ABI Prism Big Dye Terminator Ready Reaction Kit (Perkin-Elmer) and sequence samples are run on the 3700 DNA Analyzer (96 Capillary Sequencer).

FGU-CBT (SCA2-SNP) identifies a method where the region containing the SNP were PCR amplified using the primers SCA2-FP3 and SCA2—RP3. Approximately 100 ng of genomic DNA is amplified in a 50 ml reaction volume containing a final concentration of 5 mM Tris, 25 mM KCl, 0.75 mM MgCl$_2$, 0.05% gelatin, 20 pmol of each primer and 0.5 U of Taq DNA polymerase. Samples are denatured, annealed and extended and the PCR product is purified from a band cut out of the agarose gel using, for example, the QIAquick gel extraction kit (Qiagen) and is sequenced using dye terminator chemistry on an ABI Prism 377 automated DNA sequencer with the PCR primers.

In a method identified as JBLACK (SEQ/RESTRICT), two independent PCR reactions are performed with genomic DNA. Products from the first reaction are analyzed by sequencing, indicating a unique FspI restriction site. The mutation is confirmed in the product of the second PCR reaction by digesting with Fsp I.

In a method described as KWOK(1), SNPs are identified by comparing high quality genomic sequence data from four randomly chosen individuals by direct DNA sequencing of PCR products with dye-terminator chemistry (see Kwok et al., 1996). In a related method identified as KWOK(2) SNPs are identified by comparing high quality genomic sequence data from overlapping large-insert clones such as bacterial artificial chromosomes (BACs) or P1-based artificial chromosomes (PACs). An STS containing this SNP is then developed and the existence of the SNP in various populations is confirmed by pooled DNA sequencing (see Taillon-Miller et al., 1998). In another similar method called KWOK(3), SNPs are identified by comparing high quality genomic sequence data from overlapping large-insert clones BACs or PACs. The SNPs found by this approach represent DNA sequence variations between the two donor chromosomes but the allele frequencies in the general population have not yet been determined. In method KWOK(5), SNPs are identified by comparing high quality genomic sequence data from a homozygous DNA sample and one or more pooled DNA samples by direct DNA sequencing of PCR products with dye-terminator chemistry. The STSs used are developed from sequence data found in publicly available databases. Specifically, these STSs are amplified by PCR against a complete hydatidiform mole (CHM) that has been shown to be homozygous at all loci and a pool of DNA samples from 80 CEPH parents (see Kwok et al., 1994).

In another such method, KWOK (OverlapSnpDetectionWithPolyBayes), SNPs are discovered by automated computer analysis of overlapping regions of large-insert human genomic clone sequences. For data acquisition, clone sequences are obtained directly from large-scale sequencing centers. This is necessary because base quality sequences are not present/available through GenBank. Raw data processing involves analyzed of clone sequences and accompanying base quality information for consistency. Finished ('base perfect', error rate lower than 1 in 10,000 bp) sequences with no associated base quality sequences are assigned a uniform base quality value of 40 (1 in 10,000 by error rate). Draft sequences without base quality values are rejected. Processed sequences are entered into a local database. A version of each sequence with known human repeats masked is also stored. Repeat masking is performed with the program "MASKERAID." Overlap detection: Putative overlaps are detected with the program "WUBLAST." Several filtering steps followed in order to eliminate false overlap detection results, i.e. similarities between a pair of clone sequences that arise due to sequence duplication as opposed to true overlap. Total length of overlap, overall percent similarity, number of sequence differences between nucleotides with high base quality value "high-quality mismatches." Results are also compared to results of restriction fragment mapping of genomic clones at Washington University Genome Sequencing Center, finisher's reports on overlaps, and results of the sequence contig building effort at the NCBI. SNP detection: Overlapping pairs of clone sequence are analyzed for candidate SNP sites with the 'POLYBAYES' SNP detection software. Sequence differences between the pair of sequences are scored for the probability of representing true sequence variation as opposed to sequencing error. This process requires the presence of base quality values for both sequences. High-scoring candidates are extracted. The search is restricted to substitution-type single base pair variations. Confidence score of candidate SNP is computed by the POLYBAYES software.

In method identified by KWOK (TaqMan assay), the Taq-Man assay is used to determine genotypes for 90 random individuals. In method identified by KYUGEN(Q1), DNA samples of indicated populations are pooled and analyzed by PLACE-SSCP. Peak heights of each allele in the pooled analysis are corrected by those in a heterozygote, and are subsequently used for calculation of allele frequencies. Allele frequencies higher than 10% are reliably quantified by this method. Allele frequency=0 (zero) means that the allele was found among individuals, but the corresponding peak is not seen in the examination of pool. Allele frequency=0-0.1 indicates that minor alleles are detected in the pool but the peaks are too low to reliably quantify.

In yet another method identified as KYUGEN (Method1), PCR products are post-labeled with fluorescent dyes and analyzed by an automated capillary electrophoresis system under SSCP conditions (PLACE-SSCP). Four or more individual DNAs are analyzed with or without two pooled DNA (Japanese pool and CEPH parents pool) in a series of experiments. Alleles are identified by visual inspection. Individual DNAs with different genotypes are sequenced and SNPs identified. Allele frequencies are estimated from peak heights in the pooled samples after correction of signal bias using peak heights in heterozygotes. For the PCR primers are tagged to have 5'-ATT or 5'-GTT at their ends for post-labeling of both strands. Samples of DNA (10 ng/ul) are amplified in reaction mixtures containing the buffer (10 mM Tris-HCl, pH 8.3 or 9.3, 50 mM KCl, 2.0 mM $MgCl_2$), 0.25 µM of each primer, 200 µM of each dNTP, and 0.025 units/µl of Taq DNA polymerase premixed with anti-Taq antibody. The two strands of PCR products are differentially labeled with nucleotides modified with R110 and R6G by an exchange reaction of Klenow fragment of DNA polymerase I. The reaction is stopped by adding EDTA, and unincorporated nucleotides are dephosphorylated by adding calf intestinal alkaline phosphatase. For the SSCP: an aliquot of fluorescently labeled PCR products and TAMRA-labeled internal markers are added to deionized formamide, and denatured. Electrophoresis is performed in a capillary using an ABI Prism 310 Genetic Analyzer. Genescan softwares (P-E Biosystems) are used for data collection and data processing. DNA of individuals (two to eleven) including those who showed different genotypes on SSCP are subjected for direct sequencing using big-dye terminator chemistry, on ABI Prism 310 sequencers. Multiple sequence trace files obtained from ABI Prism 310 are processed and aligned by Phred/Phrap and viewed using Consed viewer. SNPs are identified by PolyPhred software and visual inspection.

In yet another method identified as KYUGEN (Method2), individuals with different genotypes are searched by denaturing HPLC (DHPLC) or PLACE-SSCP (Inazuka et al., 1997) and their sequences are determined to identify SNPs. PCR is performed with primers tagged with 5'-ATT or 5'-GTT at their ends for post-labeling of both strands. DHPLC analysis is carried out using the WAVE DNA fragment analysis system (Transgenomic). PCR products are injected into DNASep column, and separated under the conditions determined using WAVEMaker program (Transgenomic). The two strands of PCR products that are differentially labeled with nucleotides modified with R110 and R6G by an exchange reaction of Klenow fragment of DNA polymerase I. The reaction is stopped by adding EDTA, and unincorporated nucleotides are dephosphorylated by adding calf intestinal alkaline phosphatase. SSCP followed by electrophoresis is performed in a capillary using an ABI Prism 310 Genetic Analyzer. Genescan softwares (P-E Biosystems). DNA of individuals including those who showed different genotypes on DHPLC or SSCP are subjected for direct sequencing using big-dye terminator chemistry, on ABI Prism 310 sequencer. Multiple sequence trace files obtained from ABI Prism 310 are processed and aligned by Phred/Phrap and viewed using Consed viewer. SNPs are identified by PolyPhred software and visual inspection. Trace chromatogram data of EST sequences in Unigene are processed with PHRED. To identify likely SNPs, single base mismatches are reported from multiple sequence alignments produced by the programs PHRAP, BRO and POA for each Unigene cluster. BRO corrected possible misreported EST orientations, while POA identified and analyzed non-linear alignment structures indicative of gene mixing/chimeras that might produce spurious SNPs. Bayesian inference is used to weigh evidence for true polymorphism versus sequencing error, misalignment or ambiguity, misclustering or chimeric EST sequences, assessing data such as raw chromatogram height, sharpness, overlap and spacing; sequencing error rates; context-sensitivity; cDNA library origin, etc.

IX. Pharmaceutical Formulations and Routes of Administration

The therapeutic compounds of the present disclosure may be administered by a variety of methods, e.g., orally or by injection (e.g. subcutaneous, intravenous, intraperitoneal, etc.). Depending on the route of administration, the active compounds may be coated in a material to protect the compound from the action of acids and other natural conditions which may inactivate the compound. They may also be administered by continuous perfusion/infusion of a disease or wound site.

To administer the therapeutic compound by other than parenteral administration, it may be necessary to coat the compound with, or co-administer the compound with, a material to prevent its inactivation. For example, the therapeutic compound may be administered to a patient in an appropriate carrier, for example, liposomes, or a diluent. Pharmaceutically acceptable diluents include saline and aqueous buffer solutions. Liposomes include water-in-oil-in-water CGF emulsions as well as conventional liposomes (Strejan et al., 1984).

The therapeutic compound may also be administered parenterally, intraperitoneally, intraspinally, or intracerebrally. Dispersions can be prepared in glycerol, liquid polyethylene glycols, and mixtures thereof and in oils. Under ordinary conditions of storage and use, these preparations may contain a preservative to prevent the growth of microorganisms.

Pharmaceutical compositions suitable for injectable use include sterile aqueous solutions (where water soluble) or dispersions and sterile powders for the extemporaneous preparation of sterile injectable solutions or dispersion. In all cases, the composition must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (such as, glycerol, propylene glycol, and liquid polyethylene glycol, and the like), suitable mixtures thereof, and vegetable oils. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions can be brought about by including in the composition an agent which delays absorption, for example, aluminum monostearate or gelatin.

Sterile injectable solutions can be prepared by incorporating the therapeutic compound in the required amount in an appropriate solvent with one or a combination of ingredients enumerated above, as required, followed by filtered sterilization. Generally, dispersions are prepared by incorporating the therapeutic compound into a sterile carrier which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient (i.e., the therapeutic compound) plus any additional desired ingredient from a previously sterile-filtered solution thereof.

The therapeutic compound can be orally administered, for example, with an inert diluent or an assimilable edible carrier. The therapeutic compound and other ingredients may also be enclosed in a hard or soft shell gelatin capsule, compressed into tablets, or incorporated directly into the subject's diet. For oral therapeutic administration, the therapeutic compound may be incorporated with excipients and used in the form of ingestible tablets, buccal tablets, troches, capsules, elixirs, suspensions, syrups, wafers, and the like. The percentage of the therapeutic compound in the compositions and preparations may, of course, be varied. The amount of the therapeutic compound in such therapeutically useful compositions is such that a suitable dosage will be obtained.

It is especially advantageous to formulate parenteral compositions in dosage unit form for ease of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical carrier. The specification for the dosage unit forms of the invention are dictated by and directly dependent on (a) the unique characteristics of the therapeutic compound and the particular therapeutic effect to be achieved, and (b) the limitations inherent in the art of compounding such a therapeutic compound for the treatment of a selected condition in a patient.

The therapeutic compound may also be administered topically to the skin, eye, or mucosa. Alternatively, if local delivery to the lungs is desired the therapeutic compound may be administered by inhalation in a dry-powder or aerosol formulation.

Active compounds are administered at a therapeutically effective dosage sufficient to treat a condition associated with a condition in a patient. For example, the efficacy of a compound can be evaluated in an animal model system that may be predictive of efficacy in treating the disease in humans, such as the model systems shown in the examples and drawings.

The actual dosage amount of a compound of the present disclosure or composition comprising a compound of the present disclosure administered to a subject may be determined by physical and physiological factors such as age, sex, body weight, severity of condition, the type of disease being treated, previous or concurrent therapeutic interventions, idiopathy of the subject and on the route of administration. These factors may be determined by a skilled artisan. The practitioner responsible for administration will typically determine the concentration of active ingredient(s) in a composition and appropriate dose(s) for the individual subject. The dosage may be adjusted by the individual physician in the event of any complication.

An effective amount typically will vary from about 0.001 mg/kg to about 1000 mg/kg, from about 0.01 mg/kg to about 750 mg/kg, from about 100 mg/kg to about 500 mg/kg, from about 1.0 mg/kg to about 250 mg/kg, from about 10.0 mg/kg to about 150 mg/kg in one or more dose administrations daily, for one or several days (depending of course of the mode of administration and the factors discussed above). Other suitable dose ranges include 1 mg to 10000 mg per day, 100 mg to 10000 mg per day, 500 mg to 10000 mg per day, and 500 mg to 1000 mg per day. In some particular embodiments, the amount is less than 10,000 mg per day with a range of 750 mg to 9000 mg per day.

The effective amount may be less than 1 mg/kg/day, less than 500 mg/kg/day, less than 250 mg/kg/day, less than 100 mg/kg/day, less than 50 mg/kg/day, less than 25 mg/kg/day or less than 10 mg/kg/day. It may alternatively be in the range of 1 mg/kg/day to 200 mg/kg/day. For example, regarding treatment of diabetic patients, the unit dosage may be an amount that reduces blood glucose by at least 40% as compared to an untreated subject. In another embodiment, the unit dosage is an amount that reduces blood glucose to a level that is ±10% of the blood glucose level of a non-diabetic subject.

In other non-limiting examples, a dose may also comprise from about 1 micro-gram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 mg/kg/body weight to about 100 mg/kg/body weight, about 5 microgram/kg/body weight to about 500 milligram/kg/body weight, etc., can be administered, based on the numbers described above.

In certain embodiments, a pharmaceutical composition of the present disclosure may comprise, for example, at least about 0.1% of a compound of the present disclosure. In other embodiments, the compound of the present disclosure may comprise between about 2% to about 75% of the weight of the unit, or between about 25% to about 60%, for example, and any range derivable therein.

Single or multiple doses of the agents are contemplated. Desired time intervals for delivery of multiple doses can be determined by one of ordinary skill in the art employing no more than routine experimentation. As an example, subjects may be administered two doses daily at approximately 12 hour intervals. In some embodiments, the agent is administered once a day.

The agent(s) may be administered on a routine schedule. As used herein a routine schedule refers to a predetermined designated period of time. The routine schedule may encompass periods of time which are identical or which differ in length, as long as the schedule is predetermined. For instance, the routine schedule may involve administration twice a day, every day, every two days, every three days, every four days, every five days, every six days, a weekly basis, a monthly basis or any set number of days or weeks there-between. Alternatively, the predetermined routine schedule may involve administration on a twice daily basis for the first week, followed by a daily basis for several months, etc. In other embodiments, the invention provides that the agent(s) may taken orally and that the timing of which is or is not dependent upon food intake. Thus, for example, the agent can be taken every morning and/or every evening, regardless of when the subject has eaten or will eat.

X. Combination Therapy

Effective combination therapy may be achieved with a single composition or pharmacological formulation that includes both agents, or with two distinct compositions or formulations, administered at the same time, wherein one composition includes a compound of this invention, and the other includes the second agent(s). Alternatively, the therapy may precede or follow the other agent treatment by intervals ranging from minutes to months.

Various combinations may be employed, such as where "A" represents the first agent (e.g., DFMO) and "B" represents a secondary agent (e.g., sulindac), non-limiting examples of which are described below:

| | | | | | | | |
|---|---|---|---|---|---|---|---|
| A/B/A | B/A/B | A/B/B | B/B/A | A/A/B | A/B/B | B/A/A | A/B/B/B | B/A/B/B |
| B/B/B/A | B/B/A/B | A/A/B/B | A/B/A/B | A/B/B/A | B/B/A/A | | |
| B/A/B/A | B/A/A/B | A/A/A/B | B/A/A/A | A/B/A/A | A/A/B/A | | |

XI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Epidemiologic Studies: ODC +316 SNP Associations with CRC-Specific Survival

Experimental Design: The study included 440 incident CRC cases from the population-based UC Irvine Gene-Environment Study of Familial CRC (diagnosed 1994-1996 with follow-up through March 2008). The primary outcome was CRC-specific survival (CRC-SS) dependent on ODC genotype (GG vs. AA/GA). In human colon cancer cell lines, ODC allele-specific binding of E-box transcription factors was determined via western blotting and chromatin immunoprecipitation (CHIP) assays. ODC allele-specific promoter activity was determined using promoter constructs in combination with vectors expressing either the transcriptional activator c-MYC or the repressor MAD1.

Results: Genotype-specific survival differences among CRC cases were limited to colon cancer cases: compared to ODC GG genotype cases (HR=1.00, reference) the adjusted CRC-SS hazards ratio (HR) was 2.31 (1.15-4.64) for ODC GA cases and 3.73 (0.93-14.99) for ODC AA cases (P-trend=0.006). In colon cancer cells, the ODC +316 SNP, flanked by two E-boxes, predicts ODC promoter activity. The E-box activator -MYC and repressors MAD1 and MAD4 preferentially bind to minor A-, compared to major G-, alleles in cultured cells.

Study population. We studied incident cases of invasive CRC enrolled in the University of California, Irvine Gene-Environment Study of Familial Colorectal Cancer (Peel et al., 2000; Zell et al., 2007) during 1994-1996 with follow-up through March 2008. The parent study was designed to determine the incidence of HNPCC in a large, population-based cohort of colorectal cancer cases. Participants were identified through the population-based cancer registries of the Cancer Surveillance Program of Orange County/San Diego Imperial Organization for Cancer Control using the April 2008 data file. In the parent study (Peel et al., 2000), all subjects with CRC diagnosed at all ages in Orange County, CA, from 1994 to 1996 were ascertained. All subjects diagnosed in San Diego and Imperial Counties, CA, at ages <65 y between 1994 and 1995 were also ascertained. Cases were then contacted if they were eligible for the study (alive at the time ascertained and having a contact address) and if their physicians did not deny permission to contact. At the time of study entry, cases signed a consent form allowing for blood draws and the release of medical information. This study was approved by the UC Irvine Institutional Review Board (#93-257). Clinical and demographic data including vital status and follow-up were obtained through linkage to the regional cancer registry databases as previously described (Peel et al., 2000; Zell et al., 2007; Zell et al., 2008). Tumor, node, metastasis (TNM) staging determination was derived from existing AJCC codes where available and conversion of extent of disease codes, as previously reported (Le et al., 2008). Family history of cancer in a first-degree relative was ascertained by self-reporting during a telephone interview conducted at enrollment (Zell et al., 2008; Ziogas and Anton-Culver, 2003). Twenty-two cases with hereditary non-polyposis colon cancer (HNPCC), as defined by Amsterdam criteria, were identified and excluded from the analysis. The median time from CRC diagnosis until study entry (i.e., date of family history interview) was 16 months (95% CI 12-23 months).

DNA extraction and ODC +316 SNP genotyping. DNA was extracted from 2.0 mL red blood cell clot samples using the QIAGEN QIAamp DNA Midi or Mini Kits, (Qiagen) following the manufacturer's instructions. Genotyping of the ODC +316 SNP was conducted using oligonucleotide primers designed to amplify a 172-bp fragment containing the polymorphic base at +316 (Applied Biosystems, Foster City, Calif.). Allele-specific TaqMan probes were synthesized with different 5' labels (6-carboxyflourescein or VIC) and the same 3' quencher dye (6-carboxytetramethylrhodamine) (23). Each PCR reaction (5 µL total) contained 10 ng of participant DNA, 30 pmol of each primer, 12.5 pmol of each TaqMan probe, and 1× TaqMan Universal PCR Master Mix (Applied Biosystems, Foster City, Calif.), as previously reported (Martinez et al., 2003; Guo et al., 2000).

Statistical analysis—population-based study. Sample size was determined based on an estimated 1:1 ratio of ODC GG genotype to ODC GA/AA genotype (Martinez et al., 2003; Barry et al. 2006; Hubner et al., 2008; Guo et al., 2000). Prior analysis of data from 1154 colon and rectal cancer cases in the UC Irvine Gene-Environment Study of Familial CRC revealed that 10-year CRC-specific survival approximated 66% (Zell et al., 2008). The inventors proposed a 15% or greater difference in CRC-specific survival based on ODC genotype alone for our sample size calculations. Thus, 315 total subjects were needed to detect the proposed difference in 10-year CRC-specific survival between two groups at 5% significance level with 80% power: 55% in group 1 vs. 70% in group 2. 440 of 481 DNA samples were successfully genotyped. 41 cases (8.5%) resulted in an undetermined ODC +316 genotype due to low DNA concentration and/or poor DNA quality, however no clinicopathologic differences were observed between the successfully genotyped and unsuccessfully genotyped cases. Thus the study was sufficiently powered to address the primary endpoint.

Comparisons of demographic, clinical, and pathologic variables among colon and rectal cases were done using Pearson chi-square statistic or Fisher's exact test for nominal variables and Student t-test for continuous variables. Colorectal cancer-specific survival was defined as mortality from CRC itself, and data censoring occurred in the following instances: alive at the end of follow-up, loss to follow-up, or death from any cause other than CRC. Overall survival (OS) was defined with mortality from any cause. Survival curves were constructed for colon and rectal cancer cases using the Kaplan-Meier method and analyzed with the log rank test for univariate analyses. Cox proportional hazards modeling was performed for all CRC cases, colon cancer cases, and rectal cancer cases using time since diagnosis to profile the adjusted risk of overall and CRC-specific death based on ODC genotype. The effects of ODC genotype (GG, GA, or AA) on survival were analyzed in the Cox models with adjustment for the following covariates: age, gender, ethnicity, family history of CRC, TNM stage at diagnosis, tumor site within the colon, histologic subtype, treatment with surgery, radiation therapy, and chemotherapy. Each variable in the model was coded using dummy variables. All analyses were conducted using SAS 9.2 statistical software (SAS Institute, Cary, N.C.). Statistical significance was assumed for a 2-tailed P value <0.05.

Example 2

Experimental Studies: ODC +316 SNP Regulation in Colon Cancer Cells

Cell culture. The human colon cancer cell lines HT29 and HCT116 were maintained in McCoy's 5A medium (Invitrogen, Carlsbad, Calif.). All media used were supplemented with 10% FBS plus 1% penicillin/streptomycin solution (Invitrogen, Carlsbad, Calif.). Cultures were maintained at 37° C. in a humidified atmosphere of 5% $CO_2$.

Genotyping assay. DNA samples from HT29 and HCT116 cells were subjected to a PCR-RFLP procedure to detect the polymorphic PstI site. Sequences were amplified by PCR, using the following primers: 5'-TCTGCGCTTC-CCCATGGGGCT-3' (SEQ ID NO:1) and 5'-TTTCCCAAC-CCTTCG-3' (SEQ ID NO:2). Each reaction contained ~1 µl DNA, 4 pmol of each primer, 12.5 µl 2×PCR PreMixes buffer "G" (EPICENTRE Biotechnologies, Madison, Wis.) and 0.5 unit of Taq DNA polymerase, in a final volume of 25 µl. The expected size of the PCR product was 351 bp. After amplification, 10-20 µl of the PCR product were digested with 10 units of PstI in 30 µl for 2 hours at 37° C. DNA from HT29 cells (GA), containing the PstI site, yielded two fragments of 156 and 195 bp.

Western blot analysis. Cells were harvested, lysed and proteins were separated on a 12.5% SDS-PAGE gel. Proteins were transferred by electrophoresis onto a Hybond-C membrane. The membrane was blocked with Blotto A (5% blocking grade dry milk in TTBS solution) and probed using 1:300 dilutions of primary antibodies (Santa Cruz Biotechnology, Santa Cruz, Calif.) in Blotto A. Primary antibodies were incubated at 4° C. overnight, followed by incubation with an appropriate HRP-tagged secondary antibody (1:1000 dilution) for 1 hour at room temperature. Chemiluminescent detection was conducted using ECL Western Detection reagent (Amersham Biosciences, Piscataway, N.J.) and exposed on Biomax XAR film (Kodak).

Chromatin immunoprecipitation (CHIP). CHIP assays were performed using a commercial kit, as recommended by the manufacturer (Upstate Biotech, Lake Placid, N.Y., USA). Briefly, cells were treated with 1% formaldehyde to crosslink DNA and proteins, and DNA-protein complexes were disrupted by sonication to lengths between 200 to 1000 bp. Lysates were diluted 10-fold with immunoprecipitation (IP) dilution buffer containing protease inhibitors. Antibodies for c-MYC, MAD1 and MAD4 (Santa Cruz Biotechnology, Santa Cruz, Calif.) were used to precipitate chromatin, while additional sample was left as a minus-antibody (−Ab) control. Samples were immunoprecipitated overnight at 4° C. with rotation. Immune complexes were obtained by adding 60 ul of salmon sperm DNA/protein A Agarose slurry and incubating for an hour at 4° C. with rotation followed by gentle centrifugation (1000 rpm, 1 min). Protein A agarose pellets were washed with low salt buffer, high salt buffer, LiCl buffer and TE buffer. Then the complexes were eluted by adding 250 μl elution buffer (0.1M NaHCO$_3$, 1% SDS) twice, and DNA-protein crosslinks were reversed with 0.2 M NaCl by heating at 65° C. for 4 hours for all samples, including the input DNA and −Ab DNA controls. DNA was resuspended in 30 ul of ddH2O. For visualization of PCR product and its size, standard PCR reactions were carried out. The sequences of ODC primers used for PCR were 5'-CCTGGGCGCTCTGAGGT-3' (SEQ ID NO:3) (17mer) and 5'-AGGAAGCGGCGCCT-CAA-3' (SEQ ID NO:4) (17mer). Quantitative real-time PCR was performed using TaqMan gene expression assays kit (Applied Biosystems, Foster City, Calif.) on an ABI7700 sequence detection system. Details for the computation of relative binding can be found on the manufacturer's web site (http://www.appliedbiosystems.com/).

Transient transfections. Transient transfections were preformed using LipofectAMINE reagent (Invitrogen, Carlsbad, Calif.) according to the manufacturer's protocol, as detailed in the supplementary file. HCT116 and HT29 cells were transfected with 1 μg of pGL3-ODC/A or pGL3-ODC/G plasmids (Martinez et al., 2003) along with 0.01 μg of Renilla-TK plasmid. The Renilla-TK plasmid was purchased from Promega (Madison, Wis.) and used as a transfection efficiency control in all promoter-reporter transfection experiments. For c-MYC experiments, ODC pGL3-plasmids were co-transfected with either pcDNA 3.0 or CMV-c-MYC expression vector (OriGene, Rockville, Md.). For MAD1 experiments, the ODC plasmids were co-transfected with either pcDNA 3.1 or pcDNA-MAD1. For c-MYC and MAD1 co-transfection, ODC promoter reporter constructs were prepared which contain the first 1.6 Kb of the ODC gene cloned into a pGL3 vector. The constructs included E-box 1 (−485 to −480 bp) intact (wt E-box 1) or deleted (mut E-box 1). Additionally, both variants of the +316 ODC SNP were used, creating a total of 4 different constructs. After 6 hours of incubation, cells were supplemented with complete medium containing 20% FBS and left to grow overnight. The next day after transfection 20% FBS-containing complete medium was replaced with 10% FBS-containing medium. 48 hours after transfection, cells were washed with PBS and lysed in Passive Lysis Buffer from the Dual Luciferase Assay kit (Promega, Madison, Wis.). Dual luciferase activities were measured using a Turner Designs TD-20/20 luminometer, as described by the manufacturer, and presented as relative luciferase units (RLU). Experiments were preformed in triplicates and repeated at least 2 times.

Statistical analysis—experimental studies. For transient transfection experiments, two-sample t-tests were used (Microsoft Excel Microsoft Corp., Redmond, Wash.). The effect of c-MYC expression on ODC allele-specific promoter activity was examined in HT29 colon cancer cells using ODC promoter constructs differing by the presence of the first E-box element: (a) wild type (wt) E-box1+316 G, (b) mutant (mut) E-box1 +316 G, (c) wt E-box1 +316 A, and (d) mut E-box1 +316 A. For each promoter construct, two-sample t-tests were used to compare promoter activity between cells co-transfected with pcDNA3.0 plasmid versus those transfected with the CMV-c-MYC expression vector. Similarly, to examine the effect of MAD1 expression on ODC allele-specific promoter activity, two-sample t-tests were used to compare the effect of promoter activity in promoter constructs co-transfected with pcDNA3.1 plasmid versus those transfected with pcDNA-MAD1 plasmid. Statistical significance was assumed for a 2-tailed P value <0.05.

Example 3

Differential Affects of ODC1 Genotype

This study involves analysis of patient data from the multicenter phase III colon adenoma prevention trial (Meyskens et al., 2008). 375 patients were enrolled, and the study was halted by the Data Safety Monitoring Board (DSMB) after 267 patients completed end-of-study colonoscopies (due to the study meeting its efficacy endpoints). The DSMB monitored all safety and efficacy endpoints. Blood specimens were collected on 228 consenting study patients for genotyping analysis after November 2002 (including 159 of 246 patients randomized before, and 69 of 129 patients randomized after this date), when the protocol was modified in light of data demonstrating the importance of the ODC1 SNP (2). ODC1 (rs2302615) genotyping was conducted on patient-derived genomic DNA using allele-specific TaqMan probes as described previously (Guo et al., 2000). Rectal tissue polyamine content was determined as described previously (Meyskens et al., 1998; Seiler and Knodgen, 1980), using 3 of 8 randomly selected rectal mucosal biopsy specimens. Tissue polyamine response was performed for response values ranging from 25% to 45%.

ODC1 genotype was analyzed under a dominant model: AA/GA vs. GG patients. Wilcoxon Rank Sums tests were performed on non-normally distributed continuous variables across two genotype groups. Chi-square tests or Fisher's Exact Test were utilized to assess the association between baseline categorical variables and genotype group. Log binomial regression was performed on the primary outcome (adenoma recurrence) with predictors: treatment group, age, gender, race (Caucasian vs. other), aspirin usage, ODC1 genotype (in the dominant model), and a term representing the treatment by genotype interaction. For secondary outcomes (rectal tissue polyamine response, toxicities), the effects of treatment group, genotype, and interaction between treatment and genotype were examined using full log binomial models. Statistical analyses were conducted using SAS 9.2 statistical software (SAS Inc., Cary, N.C.). Patients signed informed consent for trial inclusion and specimen retrieval/analysis. The study was approved after full committee review by the UC Irvine institutional review board (IRB protocol #2002-2261) and review by each of the local IRBs at participating study sites.

ODC1 genotype distribution was: 126 GG (55%), 87 GA (38%), and 15 AA (7%). Baseline clinical characteristics revealed differences, as shown in Table 1. The relative risk (RR) for adenoma recurrence related to treatment after adjustment in the full regression model was 0.39 (95% CI 0.24-0.66). Among patients receiving placebo or treatment, respectively, ototoxicity occurred in 23% vs. 22% of ODC1 GG patients, 20% vs. 21% of ODC1 GA patients, and 0% (0 of 7) vs. 57% (4 of 7) of ODC1 AA patients.

TABLE 1

Clinical Characteristics of all Subjects at Baseline (n = 228) by ODC1 Genotype.

|  | ODC1 AA/GA genotype (n = 102) | ODC1 GG genotype (n = 126) | P* |
|---|---|---|---|
| Mean Age (years ± Standard Deviation) | 60.2 ± 8.4 SD | 62.6 ± 8.7 SD | 0.024† |
| Gender (n, %) | | | |
| Male | 77 (75%) | 96 (76%) | 0.90 |
| Female | 25 (25%) | 30 (24%) | |
| Race (n, %) | | | |
| White | 84 (82%) | 107 (85%) | 0.007‡ |
| Black | 3 (3%) | 4 (3%) | |
| Hispanic | 4 (4%) | 12 (10%) | |
| Asian | 9 (9%) | 1 (1%) | |
| Other | 2 (2%) | 2 (2%) | |
| Treatment group (n, %) | | | |
| Eflornithine + sulindac | 46 (45%) | 71 (56%) | 0.09 |
| Placebo | 56 (55%) | 55 (44%) | |
| Low-dose aspirin use (n, %) | | | |
| Yes | 44 (43%) | 54 (43%) | 0.97 |
| No | 58 (57%) | 72 (57%) | |
| Median no. (with minimum-maximum) | 2.00 (1.11) | 2.00 (1.16) | 0.41† |
| Location of largest prior polyp (n, %) | | | |
| Rectum | 26 (25%) | 23 (18%) | 0.19 |
| Colon | 76 (75%) | 103 (82%) | |
| Prior polyp histology (n, %) | | | |
| Tubular | 76 (75%) | 99 (79%) | 0.03‡ |
| Adenoma-NOS | 6 (6%) | 8 (6%) | |
| Tubulovillous | 10 (10%) | 17 (13%) | |
| Villous | 7 (7%) | 1 (1%) | |
| Carcinoma in-situ | 3 (3%) | 0 (0%) | |
| Tubular adenoma, high-grade dysplasia | 0 (0%) | 1 (1%) | |
| Largest polyp ≧1 cm (n, %) | 25 (25%) | 40 (32%) | 0.23 |
| Treatment rendered for prior polyp (n, %) | | | |
| Complete endoscopic removal | 92 (90%) | 117 (93%) | 0.47 |
| Surgery | 10 (10%) | 9 (7%) | |
| Baseline tissue polyamine content§ (median, nmol/mg protein, range) | | | |
| Putrescine | 0.47 (0.01-4.60) | 0.56 (0.01-5.29) | 0.48† |
| Spermidine | 1.99 (0.76-9.18) | 2.17 (1.05-8.97) | 0.08† |
| Spermine | 6.82 (2.29-19.86) | 7.29 (2.72-22.85) | 0.23† |
| Spermidine:Spermine ratio | 0.30 (0.19-0.98) | 0.31 (0.19-0.76) | 0.23† |

*p-value for the $\chi^2$ test is listed unless noted otherwise.
†p-value for the Wilcoxon Rank Sums test.
‡p-value for the Fisher Exact test.
§Tissue polyamine data missing for 1 subject with ODC1 GG genotype and 1 subject with ODC1 AA/GA genotype

TABLE 2

Multivariate Overall Survival and Colorectal Cancer-Specific Survival Analysis for Colorectal Cancer Cases Based on ODC1 Genotype.

|  | ODC1 Genotype | | |
|---|---|---|---|
|  | GG | GA/AA | P |
| Overall mortality | | | |
| Number of events | 47 | 62 | |
| Number at risk | 208 | 192 | |
| Unadjusted HR (95% CI) | 1 (reference) | 1.57 (1.07-2.29) | 0.020 |
| Adjusted HR (95% CI)* | 1 (reference) | 1.58 (1.07-2.34) | 0.021 |
| CRC-specific mortality | | | |
| Number of events | 22 | 37 | |
| Number at risk | 208 | 192 | |
| Unadjusted HR (95% CI) | 1 (reference) | 1.97 (1.16-3.34) | 0.012 |
| Adjusted HR (95% CI)* | 1 (reference) | 2.02 (1.17-3.50) | 0.012 |

Abbreviation: 95% CI, 95% confidence interval.

*Includes stratification for stage (I, II, III) and adjustment for age (y), gender, ethnicity, family history of colorectal cancer, TNM stage at diagnosis, tumor site within the colorectum, histologic subtype, treatment with surgery, radiation therapy, and chemotherapy.

TABLE 3

Incidence of Events after Randomization and Stratified by ODC1 Genotype (Dominant Model).

|  | Placebo (n = 111) | | Eflornithine/Sulindac (n = 117) | | |
| --- | --- | --- | --- | --- | --- |
|  | ODC1 GG | ODC1 GA or AA | ODC1 GG | ODC1 GA or AA | P* |
| Any adenoma recurrence Any adverse event - no. of patients with adverse events (%) | 22/44 (50) | 18/53 (34) | 7/64 (11) | 9/42 (21) | <0.0001 |
| Cardiovascular events[†] no. of patients (%) | 8/55 (15) | 8/56 (14) | 13/71 (18) | 9/46 (20) | 0.30 |
| Gastrointestinal events[‡], no. of patients (%) | 4/55 (7) | 8/56 (14) | 9/71 (13) | 7/46 (15) | 0.54 |
| Hearing loss at least 15 dB at ≧2 frequencies, no. of patients (%) | 10/44 (23) | 9/52 (17) | 14/63 (22) | 11/41 (27) | 0.26 |

*P-value for the likelihood ratio test for treatment effect (eflornithine and sulindac vs. placebo) on adenoma recurrence in the full model which includes age, gender, race/ethnicity, aspirin usage, treatment, genotype, and treatment and genotype interaction as covariates. A statistically significant interaction was detected in the full model for adenoma recurrence (P = 0.038); no interaction was detected for cardiovascular toxicity, gastrointestinal toxicity, or ototoxicity.
[†]Cardiovascular events included coronary artery disease, myocardial infarction, cerebrovascular accident, congestive heart failure, and chest pain.
[‡]Gastrointestinal events included gastrointestinal bleeding (from any region) such as rectal bleeding, upper gastrointestinal bleeding, hematochezia, or occult blood in the stool.

TABLE 4

Efficacy and Adverse Events and the ODC1 + 316 SNP.

|  | Placebo (N = 111) | | | DFMO/Sulindac (N = 117) | | | |
| --- | --- | --- | --- | --- | --- | --- | --- |
|  | ODC GG (N = 55) | ODC GA (N = 48) | ODC AA (N = 8) | ODC GG (N = 71) | ODC GA (N = 39) | ODC AA (N = 7) | P |
| Any adenoma recurrence (%) | 22/44 (50) | (35) | (29) | 7/64 (11) | (14) | (57) | <0.0001 |
| Cardiovascular events no. of patients (%)a | 8/55 (15) | 7/48 (15) | 1/8 (13) | 13/71 (18) | 7/39 (18) | 2/7 (29) | 0.37 |
| Gastrointestinal events no. of patients (%)b | 4/55 (7) | 8/48 (17) | 0/8 (0) | 9/71 (13) | 5/39 (13) | 2/7 (29) | 0.45 |
| Hearing loss at least 15 dB at ≧2 frequencies, no. of patients (%)c | 10/44 (23) | 9/45 (20) | 0/8 (0) | 14/63 (22) | 7/34 (21) | 4/7 (57) | 0.020 |

All of the methods disclosed and claimed herein can be made and executed without undue experimentation in light of the present disclosure. While the methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references to the extent that they provide exemplary procedural or other details supplementary to those set forth herein, are specifically incorporated herein by reference.

U.S. Pat. No. 3,647,858
U.S. Pat. No. 3,654,349
U.S. Pat. No. 4,330,559
U.S. Pat. No. 4,413,141
U.S. Pat. No. 4,582,788
U.S. Pat. No. 4,656,127
U.S. Pat. No. 4,683,194
U.S. Pat. No. 4,683,202
U.S. Pat. No. 5,814,625
U.S. Pat. No. 5,843,929
U.S. Pat. No. 5,952,174
U.S. Pat. No. 6,258,845
Alberts et al., *J. Cell. Biochem. Supp.*, (22):18-23, 1995.
AMA Drug Evaluations Annual, 1814-1815, 1994.
Babbar et al., *Biochem. J.*, 394:317-24, 2006.
Babbar et al., *J. Biol. Chem.*, 278(48):47762-47775, 2003.
Barry et al., *J. Natl. Cancer Inst.*, 98(20):1494-500, 2006.
Bedi et al., *Cancer Res.*, 55(9):1811-1816, 1995.
Bellofernandez et al., *Proc. Natl. Acad. Sci. USA*, 90:7804-8, 1993.
Bussey, *Hepatology*, 12(1):175-6. 1990
Childs et al., *Cell. Molec. Life Sci.*, 60:1394-1406, 2003.
de Arruda et al., *Expert Rev. Mol. Diagn.*, 2(5):487-496, 2002.
Derynck et al., *Nature Genetics*, 29:117-29, 2001.
DuBois et al., *Cancer Res.*, 56:733-737, 1996.
Erdman et al., *Carcinogenesis*, 20:1709-13, 1999.
European Appln. 201,184
European Appln. 237,362

European Appln. 258,017
European Appln. 50,424
European Appln. 84,796
French Appln. 2,650,840
Fultz and Gerner, *Mol. Carcinog.*, 34:10-8, 2002.
Gerner and Meyskens, *Nature Rev. Cancer*, 4:781-92., 2004.
Gerner et al., *Cancer Epidemoil. Biomarkers Prev.*, 3:325-330, 1994.
Giardiello et al., *Cancer Res.*, (57):199-201, 1997.
Guo et al., *Cancer Res.*, 60(22):6314-6317, 2000.
Halushka et al., *Nat. Genet.*, 22(3):239-247,1999.
Hanif et al., *Biochemical Pharmacology*, (52):237-245, 1996.
Hubner et al., *Clin. Cancer Res.*, 14(8):2303-9, 2008.
Ignatenko et al., *Cancer Biol. Ther.*, 5(12):1658-64, 2006.
Inazuka et al., *Genome Res*, 7(11):1094-1103, 1997.
Iwamoto et al., *Carcinogenesis*, 21:1935-40, 2000.
Johnson et al., *Nat. Genet.*, 29(2):233-237, 2001.
Ke and Cardon *Bioinformatics*, 19(2):287-288, 2003.
Keller and Giardiello, *Cancer Biol. Ther.*, 2(4 Suppl 1):S140-9, 2003.
Kingsnorth et al., *Cancer Res.*, 43(9):4035-8, 1983.
Komher, et al., *Nucl. Acids. Res.* 17:7779-7784, 1989.
Kuppuswamy, et al., *Proc. Natl. Acad. Sci. USA,* 88:1143-1147, 1991.
Kwok and Chen, *Curr Issues Mol. Biol.*, April; 5(2):43-60, 2003.
Kwok et al., *Genomics*, 23(1):138-144, 1994.
Kwok, *Annu. Rev. Genomics Hum. Genet.*, 2:235-258, 2001.
Kwok et al., *Genomics*, 31(1):123-6, 1996.
Ladenheim et al., *Gastroenterology*, 108:1083-1087, 1995.
Landegren, et al., *Science*, 241:1077-1080, 1988.
Lanza et al., *Arch. Intern. Med.*, 155:1371-1377, 1995.
Le et al., *Cancer Epidemiol. Biomarkers Prev.*, 17:1950-62, 2008.
Lipkin, *J. Cell Biochem. Suppl.*, 28-29:144-7, 1997.
Lippman, *Nat. Clin. Pract. Oncol.*, 3(10):523, 2006.
Love et al., *J. Natl. Cancer Inst.*, 85:732-7, 1993.
Lu et al., *Eukaryot Cell.*, 3(6):1544-56, 2004.
Luk and Baylin, *N. Engl. J. Med.*, 311(2):80-83, 1984.
Lupulescu, *Cancer Detect. Prev.*, 20(6):634-637, 1996.
Martinez et al., *Proc. Natl. Acad. Sci. USA*, 100:7859-64, 2003.
Matsubara et al., *Clinical Cancer Res.*, 1:665-71, 1995.
Maxam, et al., *Proc. Natl. Acad. Sci. USA*, 74:560, 1977.
McLaren et al., *Cancer Prev. Res.*, 1(7):514-21, 2008.
Meyskens et al., *Cancer Prev. Res.*, 1(1):32-8, 2008.
Meyskens et al., *J. Natl. Cancer Inst.*, 86(15):1122-1130, 1994.
Meyskens et al., *J. Natl. Cancer Inst.*, 90(16):1212-8, 1998.
Mullis et al., *Cold Spring Harbor Symp. Quant. Biol.* 51:263-273, 1986.
Muscat et al., *Cancer*, 74:1847-1854, 1994.
Narisawa et al., *Cancer Res.*, 41(5):1954-1957, 1981.
Nickerson et al., *Proc. Natl. Acad. Sci. USA,* 87:8923-8927, 1990.
Nyren et al., *Anal. Biochem.* 208:171-175, 1993.
O'Brien et al., *Molec. Carcinog.*, 41(2):120-3, 2004.
Pardali and Moustakas, *Biochimica et Biophysica Acta*, 1775:21-62, 2007.
PCT Appln. WO91/02087
PCT Appln. WO92/15712
Peel et al., *J. Natl. Cancer Inst.*, 92:1517-22, 2000.
Pegg, *Biochem.*, 234(2):249-262, 1986.
Physician's Desk Reference, Medical Economics Data, Montville, N.J., 1745-1747, 1999
Piazza et al., *Cancer Res.*, (55):3113116, 1995.
Piazza et al., *Cancer Res.*, (57):2452-2459, 1997a.
Piazza et al., *Cancer Res.*, (57):2909-2915, 1997b.
Pollard and Luckert, *Cancer Res.*, 49:6471-6473, 1989.
Prezant et al., *Hum. Mutat.*, 1:159-164, 1992.
Psaty and Potter, *N. Engl. J. Med.*, 355(9):950-2, 2006.
Rao et al., *Cancer Res.*, (55):1464-1472, 1995.
Reddy et al., *Cancer Res.*, (50):2562-2568, 1990.
Reddy et al., *Cancer Res.*, 47:5340-5346, 1987.
Rice et al., *Mol. Cancer. Ther.*, 2(9):885-92, 2003.
Roberts and Wakefield, *Proc. Natl. Acad. Sci. USA,* 100:8621-3, 2003.
Sanger et al., *J. Molec. Biol.*, 94:441, 1975.
Seiler and Knodgen, *J. Chromatogr.*, 221(2):227-235, 1980.
Simoneau et al., *Cancer Epidemiol. Biomarkers Prev.*, 17:292-9, 2008.
Simoneau et al., *J. Natl. Cancer Inst.*, 93:57-9, 2001.
Singh and Reddy, *Annals. NY Acad. Sci.*, (768):205-209, 1995.
Singh et al., *Carcinogenesis*, (15):1317-1323, 1994.
Small et al., *N. Engl. J. Med.*, 347:1135-1142, 2002.
Sokolov, *Nucl. Acids Res.* 18:3671, 1990.
Stevens et al., *Biotechniques*, 34:198-203, 2003.
Strejan et al., *Cell Immunol.*, 84(1):171-184, 1984.
Su et al., *Science*, (256):668-670, 1992.
Syvanen et al., *Genomics* 8:684-692, 1990.
Taillon-Miller et al., *Genome Res*, 8(7):748-754, 1998.
Tempero et al., *Cancer Res.*, 49(21):5793-7, 1989.
Thomas and Thomas, *J. Cell Mol. Med.*, 7:113-26, 2003.
Thompson et al., *J. Natl. Cancer Inst.*, (87):125-1260, 1995.
Ugozzoll et al., *GATA* 9:107-112, 1992.
Vane and Botting, *Adv Exp Med. Biol.*, 433:131-8, 1997.
Visvanathan et al., *J. Urol.*, 171(2 Pt 1):652-5, 2004.
Wallace, *Eur. J. Clin. Invest.*, 30:1-3, 2000.
Zell et al., *Cancer Epidemiol. Biomarkers Prev.*, 17:3134-40, 2008.
Zell et al., *Cancer Prev. Res.*, 2(3):209-12, 2009.
Zell et al., *Clin. Cancer Res.*, 15(19):6208-16, 2009.
Zell et al., *Intl. J. Cancer*, 120:459-68, 2007.
Ziogas and Anton-Culver, *Am. J. Prev. Med.*, 24:190-8, 2003.

The invention claimed is:

1. A method for the preventative or curative treatment of colorectal carcinoma in a patient comprising:
   a) obtaining results from a test that determines the patient's genotype at position +316 of at least one ODC1 promoter gene allele; and
   b) if the results indicate that the patient's genotype at position +316 of at least one allele of the ODC1 promoter gene is G, administering to the patient effective amounts of a pharmaceutical therapy comprising:
      (i) a first agent that inhibits ornithine decarboxylase (ODC) within the patient; and
      (ii) a second agent that modulates the polyamine pathway to reduce overall polyamine content within the patient when combined with the first agent.

2. The method of claim 1, wherein the second agent also increases the expression of spermidine/spermine $N^1$-acetyltransferase within the patient.

3. The method of claim 1, wherein the results are obtained by receiving a report containing said genotype or taking a patient history that reveals the results.

4. The method of claim 1, wherein the test determines the nucleotide base at position +316 of one allele of the ODC1 promoter gene of the patient.

5. The method of claim 1, wherein the test determines the nucleotide bases at position +316 of both alleles of the ODC1 promoter gene of the patient.

6. The method of claim 5, wherein the results indicate that the patient's genotype at position +316 of both alleles of the ODC1 promoter gene is GG.

7. The method of claim 5, wherein the results indicate that the patient's genotype at position +316 of both alleles of the ODC1 promoter gene is GA.

8. The method of claim 1, wherein the pharmaceutical therapy further comprises increasing the dosage of the first or the second agent if the patient was already being treated with the pharmaceutical therapy, but at a lower dosage, prior to obtaining to the results of the test.

9. The method of claim 1, wherein the pharmaceutical therapy further comprises increasing the dosage of the first and the second agent if the patient was already being treated with the pharmaceutical therapy, but at a lower dosage, prior to obtaining to the results of the test.

10. The method of claim 1, wherein the first agent is α-difluoromethylornithine (DFMO).

11. The method of claim 1, wherein the second agent is a non-aspirin containing non-steroidal anti-inflammatory drug (NSAID).

12. The method of claim 11, wherein the non-aspirin containing NSAID is a selective COX-2 inhibitor.

13. The method of claim 11, wherein the non-aspirin containing NSAID is sulindac or celecoxib.

14. The method of claim 13, wherein the non-aspirin containing NSAID is sulindac.

15. A method for the treatment of colorectal carcinoma risk factors in a patient comprising:
   a) obtaining results from a test that determines the patient's genotype at position +316 of at least one ODC1 promoter gene allele; and
   b) if the results indicate that the patient's genotype at position +316 of at least one allele of the ODC1 promoter gene is G, administering to the patient effective amounts of a pharmaceutical therapy comprising:
      (i) a first agent that inhibits ornithine decarboxylase (ODC) within the patient; and
      (ii) a second agent that modulates the polyamine pathway to reduce overall polyamine content within the patient when combined with the first agent,
   wherein the method prevents the formation of new aberrant crypt foci, new adenomatous polyps or new adenomas with displasia in the patient.

16. The method of claim 15, wherein the second agent also increases the expression of spermidine/spermine $N^1$-acetyltransferase within the patient.

17. The method of claim 15, wherein the method prevents the formation of new aberrant crypt foci in the patient.

18. The method of claim 15, wherein the method prevents the formation of new adenomatous polyps in the patient.

19. The method of claim 15, wherein the method prevents the formation of new adenomas with displasia in the patient.

20. The method of claim 15, wherein the results are obtained by receiving a report containing said genotype or taking a patient history that reveals the results.

21. The method of claim 15, wherein the test determines the nucleotide base at position +316 of one allele of the ODC1 promoter gene of the patient.

22. The method of claim 15, wherein the test determines the nucleotide bases at position +316 of both alleles of the ODC1 promoter gene of the patient.

23. The method of claim 22, wherein the results indicate that the patient's genotype at position +316 of both alleles of the ODC1 promoter gene is GG.

24. The method of claim 22, wherein the results indicate that the patient's genotype at position +316 of both alleles of the ODC1 promoter gene is GA.

25. The method of claim 15, wherein the pharmaceutical therapy further comprises increasing the dosage of the first or the second agent if the patient was already being treated with the pharmaceutical therapy, but at a lower dosage, prior to obtaining to the results of the test.

26. The method of claim 15, wherein the pharmaceutical therapy further comprises increasing the dosage of the first and the second agent if the patient was already being treated with the pharmaceutical therapy, but at a lower dosage, prior to obtaining to the results of the test.

27. The method of claim 15, wherein the first agent is α-difluoromethylornithine (DFMO).

28. The method of claim 15, wherein the second agent is a non-aspirin containing non-steroidal anti-inflammatory drug (NSAID).

29. The method of claim 28, wherein the non-aspirin containing NSAID is a selective COX-2 inhibitor.

30. The method of claim 28, wherein the non-aspirin containing NSAID is sulindac or celecoxib.

31. The method of claim 30, wherein the non-aspirin containing NSAID is sulindac.

32. The method of one of claims 1 and 15, wherein the method reduces the risk of ototoxicity within the patient compared with a method that administers to the patient the same effective amount of the same pharmaceutical therapy regardless of the patient's genotype at position +316 of the ODC1 promoter gene.

33. The method of one of claims 1 and 15, wherein the patient is human.

* * * * *